US009599491B2

(12) United States Patent
Yurach et al.

(10) Patent No.: US 9,599,491 B2
(45) Date of Patent: Mar. 21, 2017

(54) TECHNIQUES FOR USE WITH TEST QUALIFICATION PROTOCOLS

(75) Inventors: Dana Yurach, Mendon, MA (US); Richard Earle, Uxbridge, MA (US); Catalin Ristache, Brasov (RO)

(73) Assignee: Waters Technologies Corporation, Milford, MA (US)

( * ) Notice: Subject to any disclaimer, the term of this patent is extended or adjusted under 35 U.S.C. 154(b) by 573 days.

(21) Appl. No.: 14/118,608

(22) PCT Filed: Jun. 13, 2012

(86) PCT No.: PCT/US2012/042199
§ 371 (c)(1),
(2), (4) Date: Mar. 4, 2014

(87) PCT Pub. No.: WO2013/112192
PCT Pub. Date: Aug. 1, 2013

(65) Prior Publication Data
US 2015/0142367 A1 May 21, 2015

Related U.S. Application Data

(60) Provisional application No. 61/497,211, filed on Jun. 15, 2011.

(51) Int. Cl.
*G06F 19/00* (2011.01)
*G01D 18/00* (2006.01)
(Continued)

(52) U.S. Cl.
CPC .............. *G01D 18/00* (2013.01); *G01N 30/00* (2013.01); *G06F 19/3412* (2013.01); *G06F 19/366* (2013.01); *H01J 49/0009* (2013.01)

(58) Field of Classification Search
CPC .............. G06F 19/3412; G06F 19/366; G06F 2201/86; H01J 49/0009; G01D 18/00; G01N 30/00; G01R 31/318555
(Continued)

(56) References Cited

U.S. PATENT DOCUMENTS 5,353,308 A 10/1994 Whetsel
5,623,500 A 4/1997 Whetsel
(Continued)

OTHER PUBLICATIONS

International Preliminary Report on Patentability dated Jan. 3, 2014.
(Continued)

*Primary Examiner* — An Do
(74) *Attorney, Agent, or Firm* — Muirhead and Saturnelli, LLC

(57) ABSTRACT

Described are techniques for performing qualification protocol testing. A qualification entity category is selected indicating a category of an entity for which a qualification test protocol is generated. One or more qualification tests are selected and included in the qualification test protocol. Test information is specified for the one or more qualification tests. The test information includes first information identifying one or more code modules executed to perform said one or more qualification tests, second information identifying test inputs to said one or more code modules, and third information specifying how to evaluate tests results from executing each of said one or more qualification tests. A qualification protocol structure including said test information is generated.

17 Claims, 23 Drawing Sheets

(51) Int. Cl.
 *G01N 30/00* (2006.01)
 *H01J 49/00* (2006.01)

(58) Field of Classification Search
 USPC ......... 702/108, 121, 123; 714/724, 733, 734
 See application file for complete search history.

(56) References Cited

U.S. PATENT DOCUMENTS 7,870,381 B2 1/2011 Hekmatpour et al.
2006/0247885 A1 11/2006 Manfredi

OTHER PUBLICATIONS

International Search Authority (ISA/US), Search Report dated Sep. 4, 2012.
"UNIFI: A Revolutionary Scientific Information System Supporting Biotherapeutic LC/High Resolution MS Studies in both Non-Regulated and GXP Laboratories," WCBP, Washington, D.C., Jan. 10-12, 2011.

TECHNIQUES FOR USE WITH TEST QUALIFICATION PROTOCOLS

CROSS REFERENCE TO RELATED APPLICATIONS

This application is a National Stage of International Application No. PCT/US2012/042199, filed Jun. 13, 2012, TECHNIQUES FOR QUALIFICATION AND MAINTENANCE OF SCIENTIFIC INFORMATION SYSTEM DEVICES, which claims priority to U.S. Provisional Application No. 61/497,211, filed Jun. 15, 2011, TECHNIQUES FOR QUALIFICATION AND MAINTENANCE OF SCIENTIFIC INFORMATION SYSTEM DEVICES, all of which are incorporated by reference herein.

BACKGROUND

Technical Field

This application generally relates to qualification protocols.

Description of Related Art

Different scientific instruments may be included in a laboratory. Such scientific instruments may include mass spectrometers (MS), instruments performing a chromatographic separation such as gas chromatographs (GC) and liquid chromatographs (LC), and the like. Operation of such instruments may be controlled using a computer system directly connected to one or more of the instruments. For example, a computer system may be used to control operation of an LC and an MS to obtain mass spectral data for a sample. The computer system may also be used in connection with performing further processing and analysis of the data, such as the mass spectra, acquired using the instruments. The data acquired from the instruments (such as raw data acquired from the instruments prior to subsequent analysis processing) as well as additional data analysis information may be stored on data storage devices of the computer system. Users may log on to the computer system with account names and passwords for authentication. Such authentication may be required prior to allowing a user to operate the instruments and also utilize software on the computer system to perform subsequent data processing and analysis of the data acquired using the instruments.

The foregoing system including the instruments and computer may be used to analyze various products and samples such as, for example, in connection with products developed by pharmaceutical companies and testing samples in hospitals and governmental laboratories. The systems performing this analysis may be regulated and required to be compliant with certain standards, guidelines, and/or regulations covering a wide variety of items. For example, the use of scientific instruments may be required to comply with government regulations for instrument qualification and validation for the same throughout the lifecycle of such instruments and other devices in a system.

SUMMARY OF THE INVENTION

In accordance with one aspect of the invention is a method for performing qualification protocol testing comprising: selecting a qualification entity category indicating a category of an entity for which a qualification test protocol is generated; selecting one or more qualification tests included in the qualification test protocol; specifying test information for said one or more qualification tests, said test information including first information identifying one or more code modules executed to perform said one or more qualification tests, second information identifying test inputs to said one or more code modules, and third information specifying how to evaluate tests results from executing each of said one or more qualification tests; and generating a qualification protocol structure including said test information. The method may include interpreting said qualification protocol structure in connection with executing said qualification test protocol thereby performing said one or more qualification tests and generating test results. The step of interpreting may include executing said one or more code modules identified in said first information and using said second information as inputs when executing said one or more code modules. The method may include evaluating said test results generated by said interpreting, said evaluating using said third information to determine a testing status of pass or fail for each of said one or more qualification tests. The qualification entity category may identify an instrument system. The instrument system may comprise a plurality of modules and the qualification protocol structure includes fourth information describing a configuration of said instrument system including said plurality of modules. The test information may include information identifying code to generate a report regarding evaluation of test results. The test information may identify one or more tests which are mandatory and one or more tests which are not mandatory and wherein the method includes deselecting at least one test that is not mandatory causing said interpreting to not execute processing for said at least one deselected test. The qualification protocol structure may be bundled with any of a new software component and an updated software component, said qualification protocol structure used to perform qualification testing for any of said new software component and said and updated software component. The new or said updated software component may be a driver used for communicating to an instrument system to operate said instrument system. The instrument system may be a scientific laboratory instrument system that performs any of liquid chromatography, gas chromatography, mass spectrometry, supercritical fluid chromatography, capillary electrophoresis, and analog to digital signal conversion and/or transmission. The qualification entity category may identify software installed on a computer system and the qualification test protocol includes one or more qualification tests for qualifying said software. The qualification protocol structure may be approved by electronically or digitally signing the qualification protocol structure. The qualification protocol structure may be exported from a first database on a first computer system and imported into a second database on a second computer system. The qualification protocol structure may be encrypted producing an encrypted structure. The method may include digitally signing the encrypted structure, and processing the digitally signed encrypted structure at the second computer system, said processing including decrypting the digitally signed encrypted structure thereby generating the qualification protocol structure and importing the qualification protocol structure into a second database on the second computer system.

In accordance with another aspect of the invention is a computer readable medium comprising code stored thereon for performing qualification protocol testing, the computer readable medium comprising code for: selecting a qualification entity category indicating a category of an entity for which a qualification test protocol is generated; selecting one or more qualification tests included in the qualification test protocol; specifying test information for said one or more qualification tests, said test information including first information identifying one or more code modules executed to perform said one or more qualification tests, second information identifying test inputs to said one or more code modules, and third information specifying how to evaluate tests results from executing each of said one or more qualification tests; and generating a qualification protocol structure including said test information.

In accordance with another aspect of the invention is a system comprising:

a plurality of scientific instruments; one or more computer systems used to control and/or communicate with the plurality of scientific instruments; a computer readable medium comprising code stored thereon for: selecting a qualification entity category indicating a category of an entity for which a qualification test protocol is generated; selecting one or more qualification tests included in the qualification test protocol; specifying test information for said one or more qualification tests, said test information including first information identifying one or more code modules executed to perform said one or more qualification tests, second information identifying test inputs to said one or more code modules, and third information specifying how to evaluate tests results from executing each of said one or more qualification tests; and generating a qualification protocol structure including said test information.

In accordance with another aspect of the invention is a computer readable medium comprising code stored thereon for performing qualification protocol testing, the computer readable medium comprising code for: importing a qualification protocol structure used in connection with executing a qualification protocol into a database, said qualification protocol structure including test information for one or more qualification tests of the qualification protocol, said test information including first information identifying one or more code modules executed to perform said one or more qualification tests, second information identifying test inputs to said one or more code modules, and third information specifying how to evaluate tests results from executing each of said one or more qualification tests; executing said one or more qualification tests, said executing including interpreting said qualification protocol structure and executing said one or more code modules identified in said first information using said second information as input when executing said one or more code modules; and generating, as a result of said executing, test results. The computer readable medium may include code for evaluating said test results, said evaluating using said third information to determine a testing status of pass or fail for each of said one or more qualification tests.

In accordance with another aspect of the invention is a method for performing qualification protocol testing comprising: importing a qualification protocol structure used in connection with executing a qualification protocol into a database, said qualification protocol structure including test information for one or more qualification tests of the qualification protocol, said test information including first information identifying one or more code modules executed to perform said one or more qualification tests, second information identifying test inputs to said one or more code modules, and third information specifying how to evaluate tests results from executing each of said one or more qualification tests; executing said one or more qualification tests, said executing including interpreting said qualification protocol structure and executing said one or more code modules identified in said first information using said second information as input when executing said one or more code modules; and generating, as a result of said executing, test results. The method may include evaluating said test results, said evaluating using said third information to determine a testing status of pass or fail for each of said one or more qualification tests.

BRIEF DESCRIPTION OF THE DRAWINGS

Features and advantages of the present invention will become more apparent from the following detailed description of exemplary embodiments thereof taken in conjunction with the accompanying drawings in which:

FIGS. 14-19 are examples of user interfaces that may be displayed in connection with a qualification wizard when executing a qualification protocol in an embodiment in accordance with techniques herein.

DETAILED DESCRIPTION OF EMBODIMENT(S)

Figure 1:
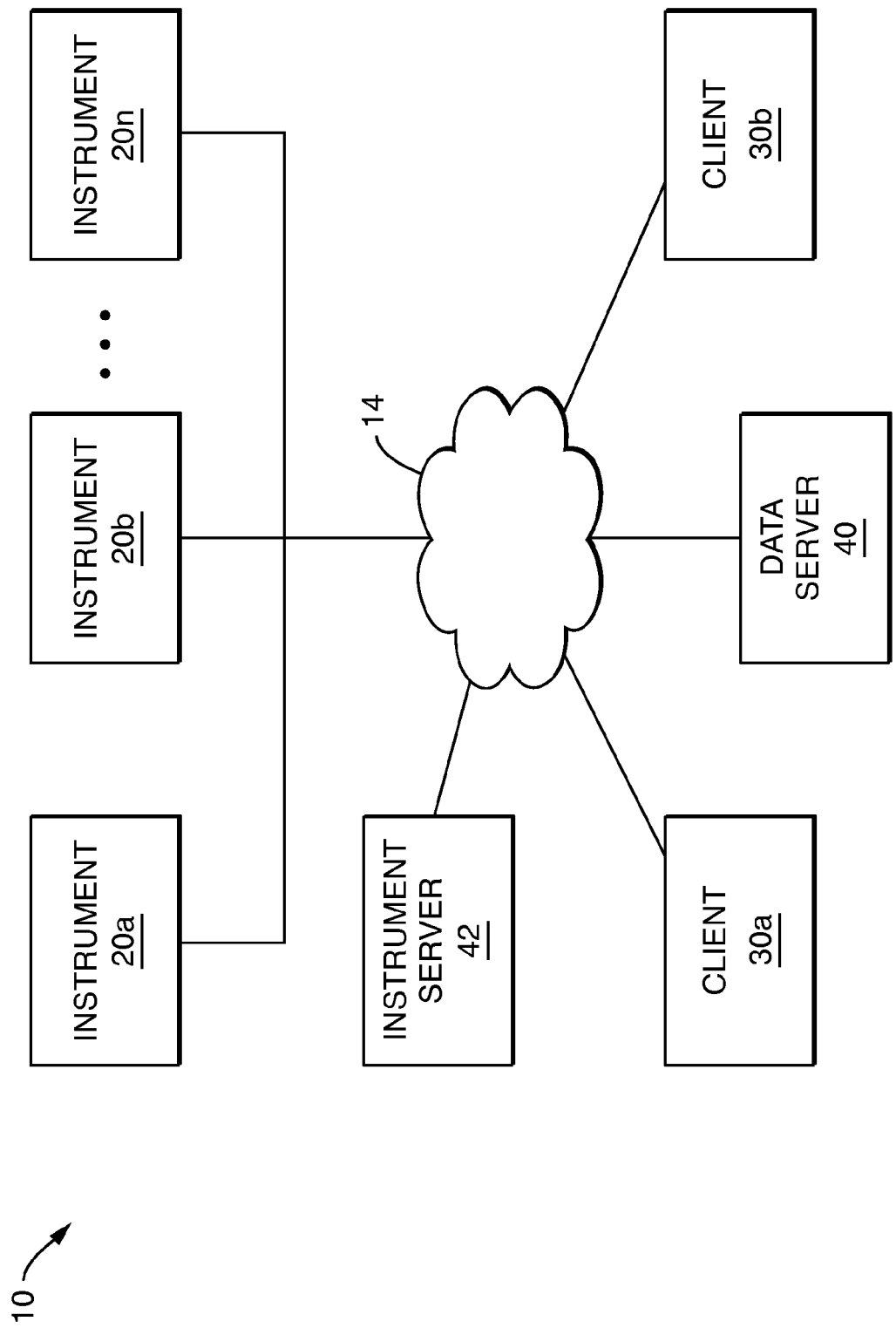
FIGS. 1 and 2A are examples of embodiments of a system that may utilize the techniques described herein.

Referring to FIG. 1, shown is an example of an embodiment of a computing environment and system that may be used in performing the techniques described herein. The computing environment illustrated in FIG. 1 is only one example of a suitable computing environment and is not intended to suggest any limitation as to the scope of use or functionality of the techniques described herein. Those skilled in the art will appreciate that the techniques described herein may be suitable for use with other general purpose and specialized purpose computing environments and configurations. Examples of well known computing systems, environments, and/or configurations include, but are not limited to, personal computers, server computers, hand-held or laptop devices, multiprocessor systems, microprocessor-based systems, programmable consumer electronics, network PCs, minicomputers, mainframe computers, virtualized computing environments (e.g., such as using virtual machines executing in a virtualized environment. For example, an embodiment may have one or more virtual machines executing on a single physical machine in a virtualized environment using virtualization software produced by VMware, Inc.), distributed computing environments that include any of the above systems or devices, and the like.

The techniques set forth herein may be described in the general context of computer-executable instructions, such as program modules, executed by one or more computers or other devices. Generally, program modules include routines, programs, objects, components, data structures, and the like, that perform particular tasks or implement particular abstract data types. Typically the functionality of the program modules may be combined or distributed as desired in various embodiments.

Included in FIG. 1 are instruments 20a-20n, client computers 30a, 30b, data server computer 40, instrument server computer 42, and a network 14. Each of the client computers 30a, 30b and server computers 40, 42 may be a standard, commercially-available computer or a special-purpose computer that may be used to execute one or more program modules. Described in more detail elsewhere herein are program modules that may be executed by client computers 30a, 30b and/or server computers 40,42 in connection with facilitating processes and practices in connection with qualification and maintenance of devices of FIG. 1. Such qualification and maintenance may relate to any aspect of the system and its components such as, for example, qualification and maintenance of the instruments 20a-20n and servers 40,42, software applications and data files stored on the data server, and the like, as may occur throughout the lifecycle of the system and components thereof. In one embodiment as described in more detail below, functionality for performing qualification and maintenance may be provided by software included in a data system used in connection with components of the illustrated system such as the instruments 20a-20n and clients 30a, 30b.

The computers 30a, 30b, 40 and 42 may operate in a networked environment and communicate with other computers, instruments, and other devices not shown in FIG. 1. The instruments 20a-20n may be scientific instruments such as liquid chromatography systems, supercritical fluid chromatography systems, capillary electrophoresis, gas chromatography systems, mass spectrometers, and other instrumentation types which may perform, for example, analog to digital signal conversion and/or transmission which are connected to the network 14 and in communication with the client computers 30a, 30b and server computers 40,42. The instruments 20a-20n may include, for example, one or more scientific instruments offered by Waters Corporation of Milford, Mass. (or any other supplier). These may also be non-networked devices such as pipettes, balances, calipers, voltmeters, pH meters or a wide variety of other devices.

As will be apparent to those of ordinary skill in the art, the techniques described herein may also be used in an embodiment in which a computer is not connected to a network. For example, a computer system utilizing the techniques herein may be directly connected to one or more instruments rather than through a network. For purposes of illustration, exemplary embodiments may be described which relate to computers used with instruments, such as scientific instruments, but should not be construed as so limited. The foregoing and other aspects and uses of techniques herein are described in more detail in following paragraphs.

The client computers 30a, 30b and server computers 40, 42 may have one or more applications executing thereon for use in connection with the instruments 20a-20n. In one embodiment, the data system may be the UNIFI™ Scientific Information System (SIS) from Waters Corporation of Milford, Mass. The techniques described herein in connection with qualification protocols and various usages may be embodied in software included in such a data system which may also provide other functionality. For example, the data system may provide functionality to collect, process, and distribute scientific information. With the data system, laboratories are able to automatically capture, secure, access, and disseminate information from any analytical technology. The data system may include functionality for an automated electronic repository that stores and manages all types of scientific data to a centralized database, offering integration with a multitude of research applications. The data system may be used in connection with controlling and managing the instruments, providing security by controlling access to activities within the data system, as well as the data and devices (e.g., instruments and computers) on the system, performing data processing, designing and using methods for data analyses and reporting, and the like. For example, the data system may include a database and may be used to provide a data-secured environment to store and retrieve data in support of regulated laboratories, using an embedded, relational database, acquire data, perform calculations, generate reports, and control a variety of instruments, perform instrument and/or software qualification, validation, and the like. An example of data that may be acquired from one of the instruments 20a-20n, where the instrument is a mass spectrometer, is a series of spectra or scans collected over time. As known in the art, a mass-to-charge spectrum is intensity plotted as a function of m/z. Each element, a single mass-to-charge ratio, of a spectrum may be referred to as a channel. Viewing a single channel over time provides a chromatogram for the corresponding mass-to-charge ratio. The generated mass-to-charge spectra or scans can be acquired and recorded on a storage medium such as a hard-disk drive or other storage media accessible to a computer. Typically, a spectrum or chromatogram is recorded as an array of values and may be stored, for example, in a database of the data system on the data server 40. The spectra stored on the data server 40 may be accessed using one of the client computers 30a, 30b such as for display, subsequent analysis (such as in connection with performance qualification or PQ described elsewhere herein), and the like. Data such as the foregoing may be stored in a data container or repository, such as a relational database or other storage facility, and remotely shared such as by multiple clients. As another example, the data system may be used in connection with providing settings for the instruments 20a-20n. For example, the data system may be used in connection with setting various parameters of a mass spectrometer and liquid chromatography system and ensuring proper access and control in connection with modifying such settings. The instrument server 42 may communicate with the one or more instruments 20a-20n to control the setting and operation of such instruments. A user may access instruments 20-20n or data such as may be stored on the data server 40 by logging onto the data system using one of the clients 30a, 30b. The data server 40 may include software of the data system for controlling access to the system using authentication techniques known in the art such as user account and passwords with one or more roles associated with the user accounts. As a security measure, roles may define types of data access and operations which an associated user is allowed to perform.

Described in following paragraphs are techniques that may be used in connection with providing software that may be included in the data system for use in connection with techniques described herein for qualification testing for any one or more different entities. For example, as described herein, such techniques may be used to create test qualification protocols used to qualify devices such as instrument systems and computers, or software on such computers. As examples, the techniques herein may be used in connection with systems providing pharmaceuticals, biopharmaceuticals, medical devices, conducting clinical trials, running certified laboratories, and the like. Systems used in connection with the foregoing may require ensuring the validity and integrity of data and results and proving compliance with applicable standards and regulations. As will be described below, the techniques herein for qualification may be used in connection with systems including instruments and components performing such applications and uses.

It will be appreciated by those skilled in the art that although devices of the system of FIG. 1 are shown in the example as communicating in a networked environment, the devices may communicate with each other and/or other devices utilizing different communication mediums and may or may not be networked together. For example, the devices of FIG. 1 may communicate with each other and/or one or more devices utilizing a network connection, and/or other type of link known in the art including, but not limited to, the Internet, an intranet, or other wireless and/or hardwired connection(s). Furthermore, as noted above, the techniques herein may be used in an embodiment with standalone computers connected directly to instruments such as without network connectivity.

Figure 2:
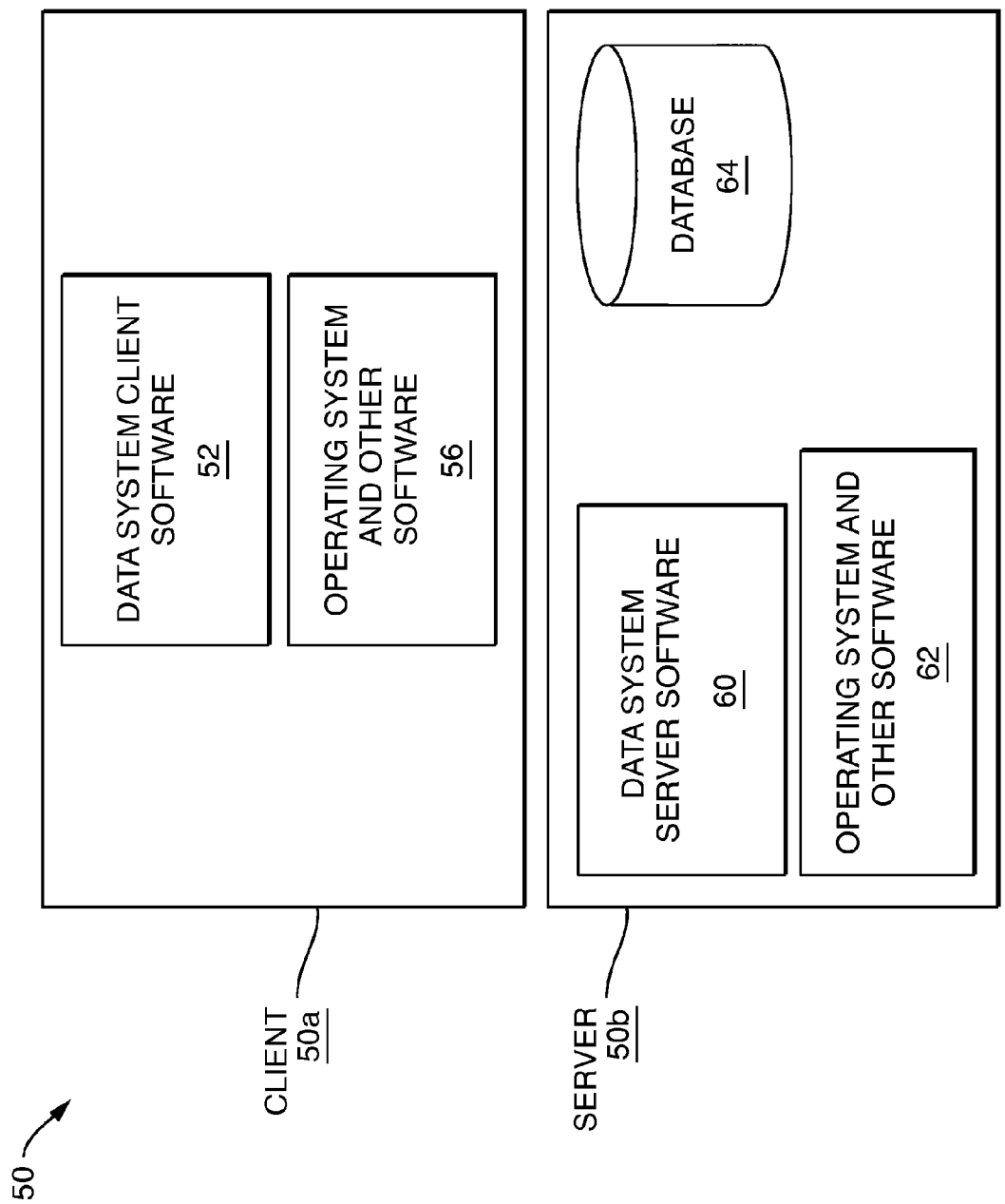
FIG. 2 is an example of components that may be included in a client and a server in an embodiment in accordance with techniques herein.

Referring to FIG. 2, shown is an example of components that may be included in a client computer 20a and data server computer 40 in an embodiment in accordance with techniques herein. The client computer 20a may include data system client software 52 and operating system and other software 56. The data system client software 52 may be, for example, the client portion of the data system described above to control and manage the instruments. In one embodiment, the client may be characterized as a thin client or a fat client. With the thin client, a majority of the application's functionality is performed by software included on the data server 40. In contrast, a thick or fat client is one in which a large portion of the application's functionality is performed by or embodied in the client software 52. The particular partitioning of functions performed by the client and data server may vary with application. Element 56 represents the operating system and possibly other software that may be on the client computer 20a. The operating system may be any one of a variety of commercially available or proprietary operating system such as, for example, a Windows-based operating system by Microsoft Corporation.

Figure 2A:
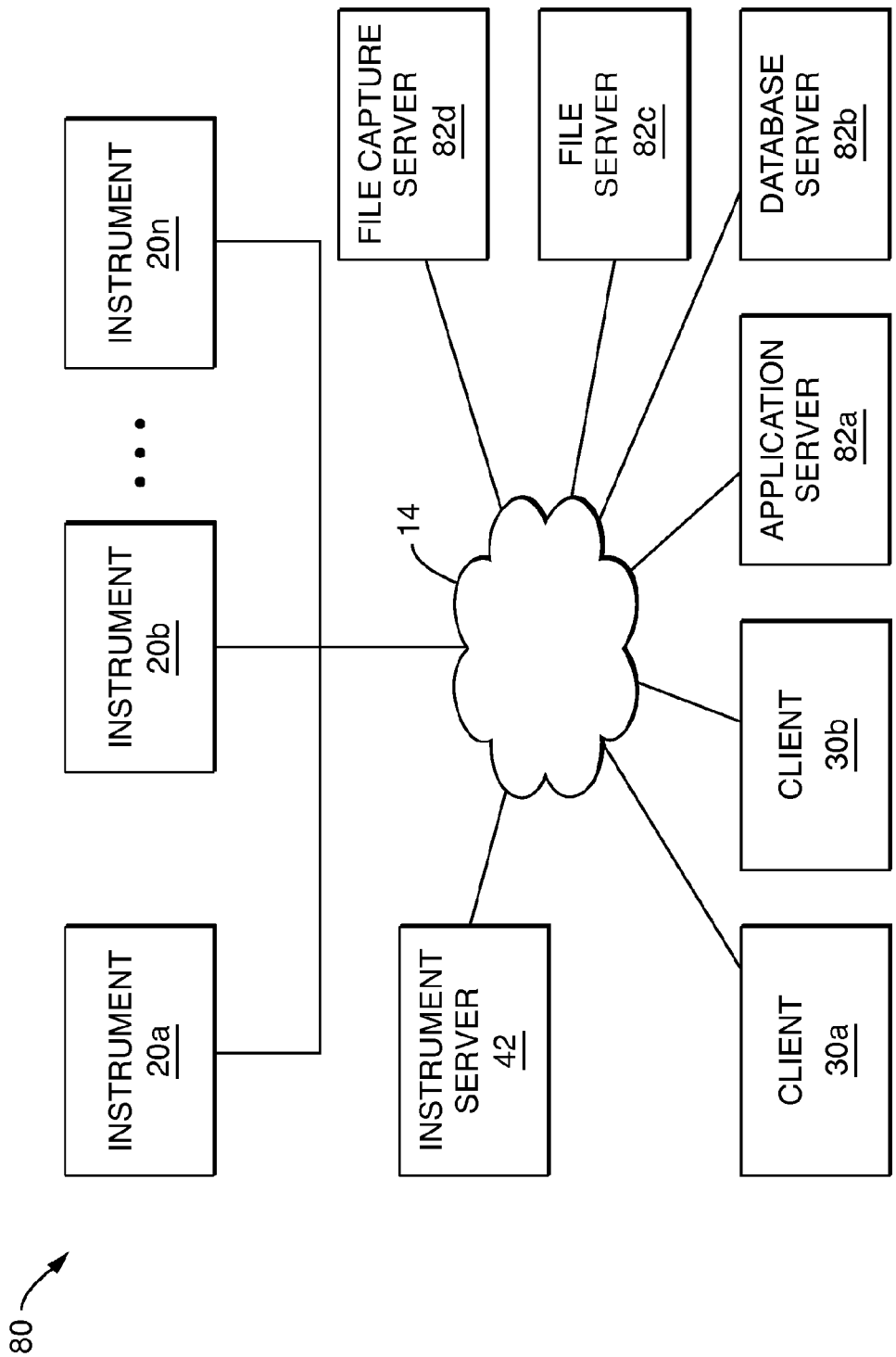

The data server 40 may include data system server software 60, a database 64, and operating system and other software 62. In some embodiments, the data server may also be distributed such that its functionality is partitioned and performed by multiple servers rather than a single server such as illustrated in FIG. 1. For example, with reference to FIG. 2A, rather than have a single data server 40 as in FIG. 1, an embodiment may have multiple servers such as, for example, a database server 82b, an application server 82a, a file server 82c, a file capture server 82d, and the like. Each of the foregoing multiple servers may perform a particular portion of the overall functionality of the single data server 40 of FIG. 1.

Referring again to FIG. 2, software represented by elements 60 and 64 may be included in the data system. The software 60 may include software implementing techniques described herein for creating qualification protocols used to performing qualification testing of devices including instruments and computers of the system. This is described in more detail in following paragraphs.

Although not illustrated in FIG. 2, each of the client 20a and data servers 40 may be a computer include one or more processing units, memory, a network interface unit, storage, and the like. Depending on the configuration and type of computer, the memory thereof may be volatile (such as RAM), non-volatile (such as ROM, flash memory, etc.) or some combination of the two. The storage may include removable and/or non-removable storage for use with computer system including, but not limited to, USB devices, magnetic or optical disks, or tape. Such storage devices have associated computer-readable media that may be utilized by the computer and may include, for example, a hard disk or CD-ROM drive, that can be accessed by the computer. Computer storage media includes volatile and nonvolatile, removable and non-removable media implemented in any method or technology for storage of information such as computer readable instructions, data structures, program modules or other data. Computer storage media includes, but is not limited to, RAM, ROM, EEPROM, flash memory or other memory technology, CD-ROM, (DVD) or other optical storage, magnetic cassettes, magnetic tape, magnetic disk storage or other magnetic storage devices, or any other medium which can be used to store the desired information and which can accessed by the computer. Each of the computers may also contain communications connection(s) to facilitate communication with other devices and components such as, by way of example, input devices and output devices. Input devices may include, for example, a keyboard, mouse, pen, voice input device, touch input device, barcode reader, etc. Output device(s) may include, for example, a display, speakers, printer, and the like. These and other devices are well known in the art.

As mentioned above, the data system client software 52 as well as server software 60 and the database 64 may comprise a data system of one or more applications used in connection with the instruments of FIG. 1. For example, such software represented by element 52 and/or 60 may be used to control operations of a liquid chromatography system or mass spectrometer, set instrument parameters used to operate the instruments, collect and store data such as results of analysis performed by the instruments, and the like. The software included in the data system may be used to manage system security of the instruments, securely provide for storing data that is used and generated by the instruments, control access to such data and the actions within the application with respect to users in accordance with roles, permissions, and the like.

The qualification protocols in accordance with techniques herein may be used in a regulated as well as a non-regulated system. For example, the qualification protocols in accordance with techniques herein may be used in connection with a regulated system meeting FDA regulatory requirements such as specified in 21 CFR parts 211, 11, 820 and many others. Such qualification protocols may be executed in connection with devices, such as instrument systems and computer systems, throughout the lifetime usage of such devices.

In connection with instrument or computer system qualification, verification activities may include, for example, documenting or providing objective evidence regarding performance of qualification processing (e.g., tests performed in connection with installation qualification (IQ), operational qualification (OQ) and/or performance qualification (PQ)), commissioning, and the like. As will be described below, an embodiment in accordance with techniques herein may be used with creating and using qualification protocols for devices.

In accordance with some systems and uses that may include providing qualification in connection with software, software verification may be generally characterized as by ISO and ASTM as confirmation, through the provision of objective evidence that specified requirements related to such qualifications have been fulfilled and a systematic approach to verify that manufacturing systems, acting singly or in combination, are fit for intended use, have been properly installed, and are operating correctly. The foregoing is an "umbrella" term that encompasses all types of approaches to assuring systems are fit for use such as qualification, commissioning and qualification, verification, system validation, or other.

In accordance with other systems and uses, software verification may be characterized as defined by the FDA in the context of its guidance *General Principles of Software Validation* (applicable within the medical device context). In this case, software verification may be characterized as providing objective evidence that the design outputs of a particular phase of the software development life cycle meet all of the specified requirements for that phase. Software verification looks for consistency, completeness, and correctness of the software and its supporting documentation, as it is being developed, and provides support for a subsequent conclusion that software is validated. Software testing is one of many verification activities intended to confirm that software development output meets its input requirements. Other verification activities include various static and dynamic analyses, code and document inspections, walk-throughs, and other techniques. Software validation is specifically defined by the FDA within its guidance for the validation of software within the medical device context as "confirmation by examination and provision of objective evidence that software specifications conform to user needs and intended uses, and that the particular requirements implemented through software can be consistently fulfilled."

Qualification may be generally be described as an action of proving and documenting that equipment or ancillary systems are properly installed, work correctly, and actually lead to the manufacturer's expected results. Qualification can be a subset of validation, but the individual qualification steps alone may not satisfy the validation requirement of establishing fit for intended use. Validation may be described as confirmation by examination and provision of objective evidence that the particular requirement for a specific intended use can be consistently fulfilled. In this case, processing is performed to validate the proper functionality of specific software operational features by automatically exercising those features in the software and collecting objective evidence of the result, effect or output.

Installation qualification (IQ) is defined by the FDA in their glossary of computer systems software development terminology glossary as establishing confidence that process equipment and ancillary systems are compliant with appropriate codes and approved design intentions, and that manufacturer's recommendations are suitably considered. More generally in connection with IQ, processing may be performed to log and record information for verifying and/or documenting that a computerized system, instrument, and the like, is installed according to written and pre-approved specifications. As an example for a chromatography system or instrument, IQ establishes that the system is received as designed, is installed properly, and verifies where the system is installed is appropriate according to the manufacturer's specifications.

Operational qualification (OQ) is defined by the FDA in their glossary of computer systems software development terminology glossary as establishing confidence that process equipment and sub-systems are capable of consistently operating within established limits and tolerances. More generally in connection with OQ, processing may be performed to log and record information for verifying and/or documenting that a computerized system, instrument and the like, operates according to written and pre-approved specifications. For example, OQ for a scientific or analytical instrument may include performing testing to ensure that the instrument operates throughout specified operating ranges. Information regarding performance, results, and the like, of tests for OQ may be recorded. As an example for a chromatography system or instrument, OQ ensures that key components or primary functionality thereof is operational according to operational specifications in the selected environment which may include its role within an integrated system. As another example, OQ for a computer system may be performed to verify calculation and reporting functionality. For example, processing a known benchmarked data set and confirming that the installed application generates equivalent results and issues equivalent reports. As an additional example, OQ for a computer system may be performed to verify security functionality facilitating compliance with 21 CFR Part 11 electronic records and signature regulation requirements. The results and outputs of such tests collected as documented evidence of correct operation of this functionality within the specific environment of the deployment for OQ of the computer system.

Performance qualification (PQ) (such as a Chromatography Data System or like data collection and/or organization system) may be defined as establishing documented evidence through appropriate testing and collection of objective evidence that the processes carried out by the integrated computerized system consistently perform as expected for the intended use. For example, PQ may verify that all components of an instrument, such as a mass spectrometer, perform properly when all components thereof are integrated. For example, PQ for an instrument may include performing tests and documenting such results to verify that an instrument is capable of performing or controlling the activities of a process the instruments is required to perform, according to written and pre-approved specifications, while in its specified operating environment. Performance testing of an instrument may be performed, for example, to demonstrate the accuracy and precision of the instrument. For example, performance testing of a liquid chromatograph or mass spectrometer may include examining results or output generated as a result of performing an injection, run or experiment using the instrument.

Qualification testing performed such as in connection with a qualification protocol may include performing any of IQ, OQ and/or PQ as may vary, for example, with device and/or regulatory requirements. To further illustrate with respect to a device that is an LC system including a pump, injector and detector, the qualification processing performed may include performing IQ, OQ and PQ tests. IQ may include, for example, ensuring that electrical connections for the installed components are operable and other factors regarding the installation environment. OQ and/or PQ tests may include, for example, tests for accuracy of temperature and flow rate such as to within an acceptable threshold level of accuracy.

Qualification of instruments, or instrument systems, is described in more detail, for example, in U.S. Pat. No. 6,456,955, Andrews et al. Automated Test Protocol, Issued Sep. 24, 2002, which is incorporated by reference herein.

The foregoing, as well as other exemplary uses of the techniques herein, are described in more detail in following paragraphs and figures.

Figure 2B:
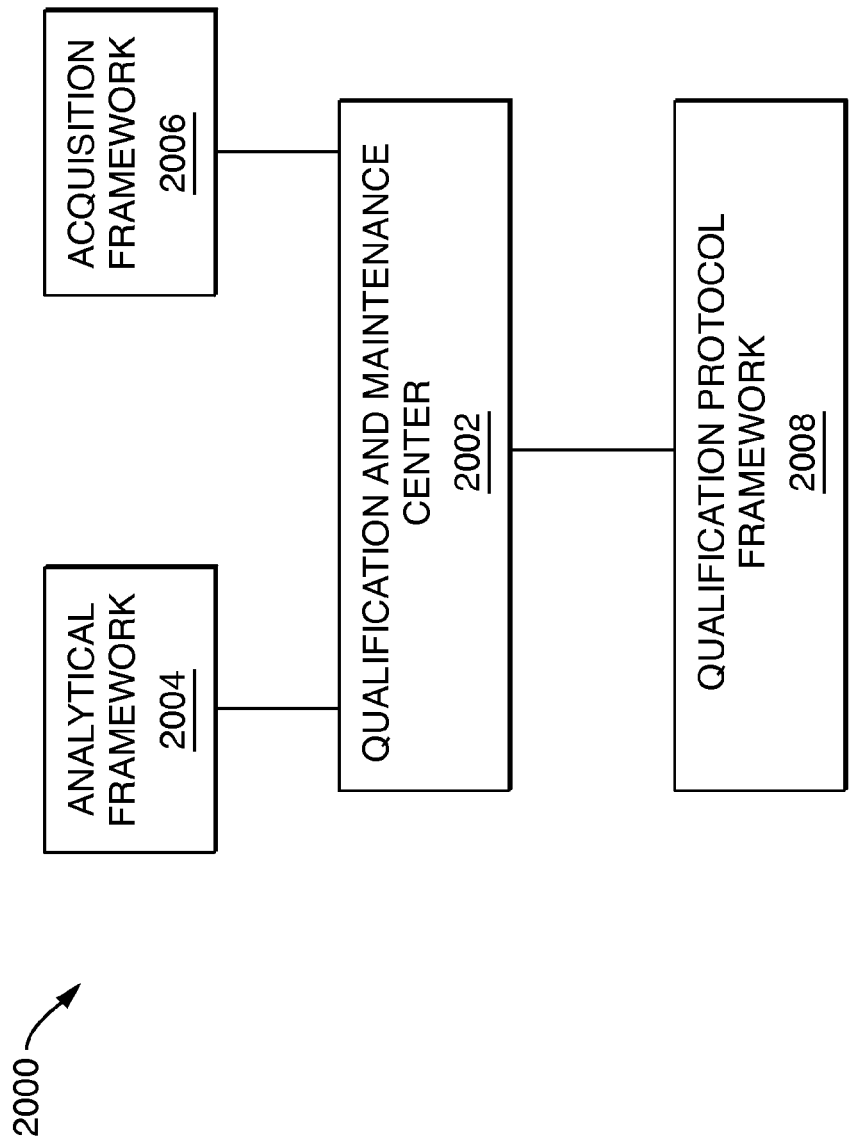
FIGS. 2B, 3 and 4 are examples illustrating elements that may be defined and used in an embodiment in accordance with techniques herein.

Referring to FIG. 2B, shown is an example of software components that may be included an embodiment in accordance with techniques herein. The example 2000 illustrates one architecture of components that may be used in an embodiment in accordance with techniques herein and includes an analytical framework 2004, acquisition framework 2006, qualification and maintenance center 2002, and qualification protocol framework 2008. The component 2002 communicates with components 2004, 2006 and/or 2008 as needed during operation. For example, component 2002 communicates with the qualification protocol framework 2008 as part of qualification test processing such as using a qualification protocol to obtain the qualification tests and instructions. Component 2002 may communicate with the analytical framework 2004 when executing the qualification tests for devices other than instruments. Component 2002 may communicate with the acquisition framework 2006 when executing the qualification tests for instruments described herein. Although not illustrated, data may be stored and/or retrieved from data containers such as databases by any of the components. For example, component 2008 may store and retrieve information about qualification protocols from a database.

The qualification protocol framework, as will be described in more detail below, utilizes a pre-defined construct, a qualification protocol structure or template, for qualifying an entity. The structure of template may be used to define the specific elements of the general process for qualifying an instrument within the qualification framework. As an example use in which the framework 2008 is used in connection with scientific and analytical instrument systems, the modules of 2000 including 2008 are architected to be used and communicate with a wide array of devices and to execute, store, and manage the qualification-related activities and results for said devices. The protocol framework may be used to generate the qualification protocol structure or template. In one particular use as described in more detail elsewhere herein, the structure or template may be bundled within or associated with the control software for a specific device. The protocol structure in accordance with techniques herein allows device manufacturers to create qualification protocols for their own devices and have these be recognized and utilized by software systems such as illustrated in FIG. 2B. In systems not utilizing techniques herein, qualification of devices may be achieved in a myriad ways and having great variation between vendors and instrument system technologies. In such systems not utilizing techniques herein, the data and results/reports may originate in disparate systems and formats that need to be maintained, managed, and secured for compliance and business reasons. For vendors who offer their customers software-based qualification solutions, the creation of automated qualification protocols may be a time-consuming process with the burden of effort on organizations which are often less familiar with devices that are not of their own manufacture. The software-based tools in use in systems not utilizing techniques herein may be varied and diverse and may require development effort as well as extensive testing. In contrast, having a system using the qualification protocols and associated structures or templates described herein allows for different device vendors, such as of instrument and computer systems, to all utilize the same components such as illustrated in FIG. 2B.

An embodiment in accordance with techniques herein may store testing data results and reports in a database as described above. Additionally, an embodiment may embed the structure or template in accordance with techniques herein with an instrument driver for ease of deployment and adaptation. Such structures may generated by a device vendor or manufacture so that the associated testing protocols may be executed at customer sites using recommended usage counters, variation limits, and the like, in accordance with vendor guidelines, compliance regulations and guidelines, and the like.

In one embodiment described in accordance with techniques herein, the qualification protocol framework 2008 may utilize a qualification protocol entity including one or more methods and qualification protocol structure or template, such as an XML-based structure. The structure or template may be interpreted at runtime when executing a testing protocol to drive the execution of verification and/or qualification activities of the testing protocol. The testing qualification protocol may be defined for a certain instrument system structure or for a certain software installation. The qualification protocol structure and specific activities as well as the interactions with other components in the system 2000 is described elsewhere herein in more detail.

In one embodiment as described in more detail below, each qualification test may be defined in configuration database tables and may have an XML descriptor configuration that holds information regarding the UI (user interface) page corresponding to each test as well as the specific configurable parameters or limits that are specific for a certain test. This may be performed to ensure the extensibility of the framework for any kind of new instruments or software configuration that will supported in the future. Each new instrument may have specific test and parameters and limits that need to be supported for qualification purposes and a system in accordance with techniques may utilize a qualification protocol framework 2009 that defines a new XML descriptor configurations for the new instrument and for each new supported test for the instruction.

In accordance with techniques herein, qualification testing may be performed for different entities. As such, an embodiment may define different categories of entities for which qualification testing is performed. In one embodiment, two general entity categories may be defined-software and instrument systems. For each entity category, there may be applicable testing categories such as IQ, OQ, and PQ. Generally the qualification tests used for instruments are different than those used for software. Furthermore, such qualification tests vary with the different instruments systems and the particular individual instruments, components or modules comprising each such instrument system. For instrument systems, there are multiple possible instrument system configurations for which qualification protocols may be associated. For example, a first instrument system may be a first LC system including a particular pump, detector and injector. A second different instrument system may also be a second LC system including the same pump but having a different detector and different injector than the first LC system. A third instrument system may be an MS instrument system including one or more modules or components customized for the particular MS instrument system. As such, applicable qualification tests may vary with entity category, instrument system, as well as the modules comprising each instrument system.

A database may be used which includes database tables having definitions and information regarding modules that may be included in an instrument system, which tests are applicable for use with which modules, instrument systems, software, and the like. For each instrument or component in a single instrument system, the database may identify applicable tests. For example, there may be some qualification tests, such as IQ tests, for each of the different components included in an instrument system. Additionally, there may be qualification tests which apply to testing an aggregation of multiple components in a single instrument system (e.g., which test the operation, performance, and other aspects of the combination of the pump, injector and detector of an LC system in combination as a single unit).

Figure 3:
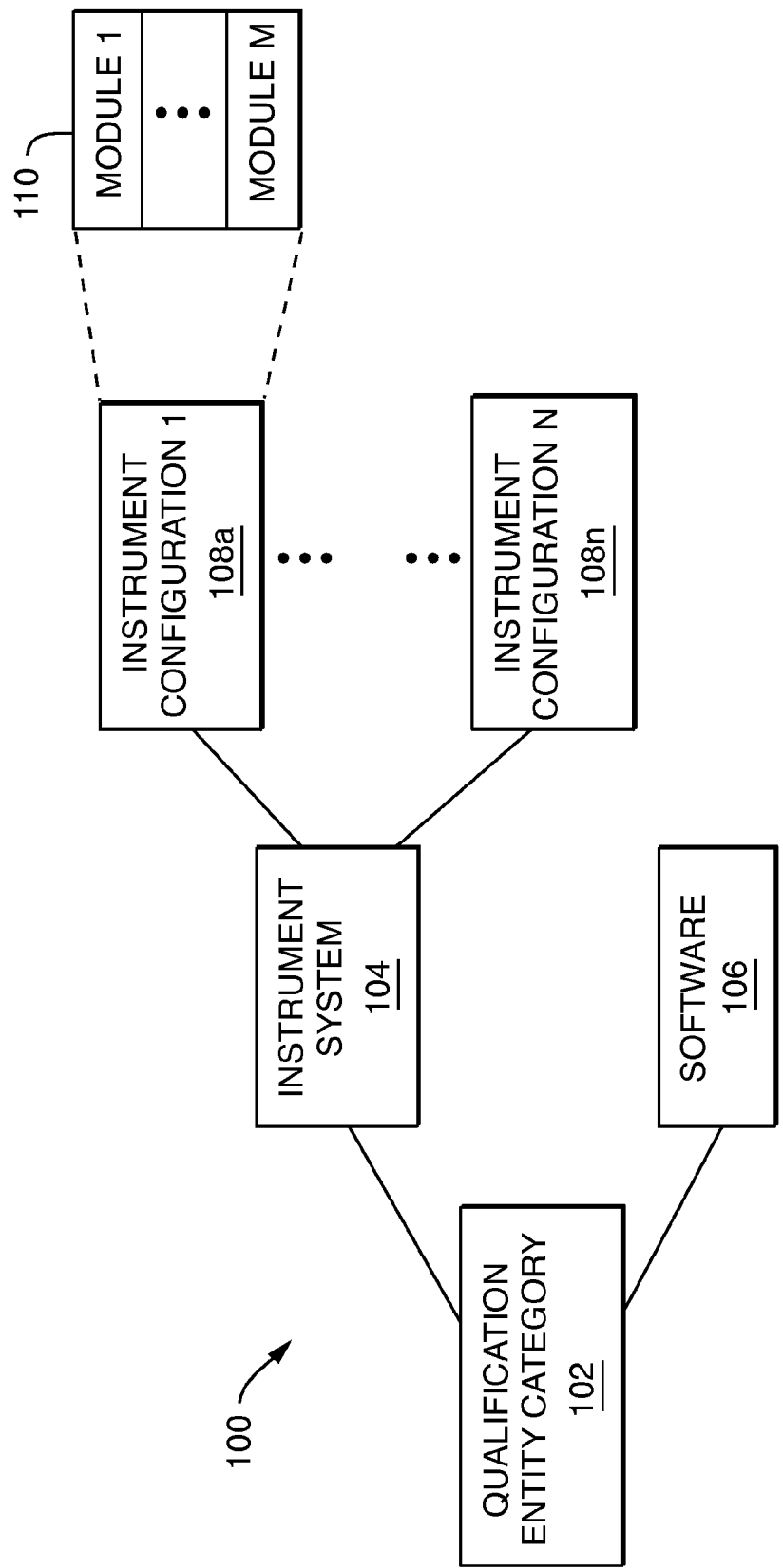

Referring to FIG. 3, shown is an example of a hierarchical structure that may be utilized in an embodiment in accordance with techniques herein for qualification entities. The example 100 includes a qualification entity category 102 which may include one or more categories each of which represents a categorical entity that for which a qualification protocol may be created. In this example, a qualification entity may be categorized as an instrument system 104 or software 106 as described above. An instrument system 104 is further defined as having any one or more instrument configurations as represented by 108a-108n. Each instrument configuration 108-108n includes one or more modules 110. It should be noted that an embodiment may include additional layers or levels in the hierarchical structure represented in FIG. 3. For example, an embodiment may include an additional layer between 104 and 108a-n listing one or more types or technologies for an instrument system. For example, an instrument system 104 may be any one of multiple types/technologies including LC, GS, MS. Each of the foregoing my then expand into one or more allowable combinations of instrument configurations 108a-n as illustrated in FIG. 3.

Figure 4:
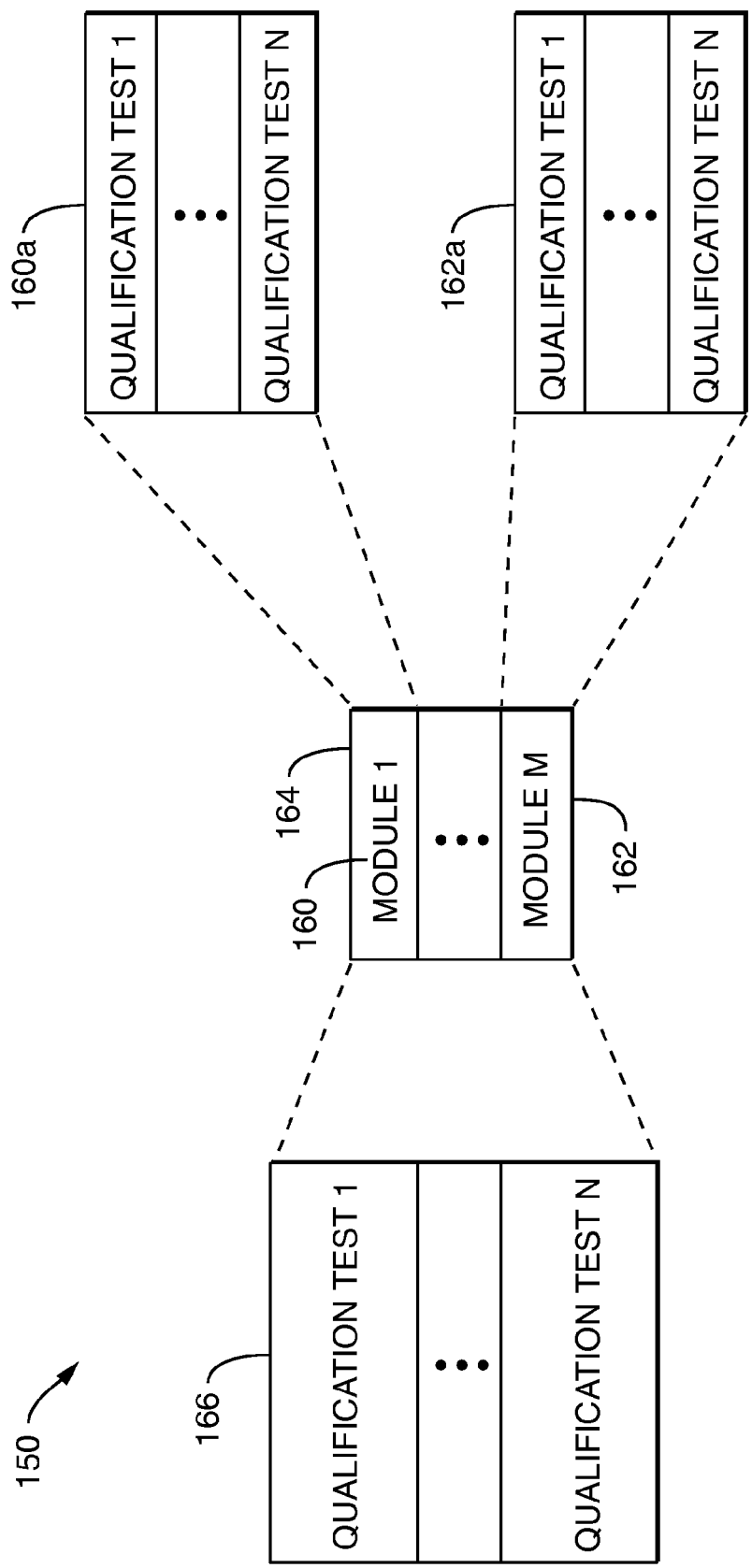

Referring to FIG. 4, shown is an example of qualification tests that may be defined in an embodiment in accordance with techniques herein. The example 150 may illustrate information and relationships as may be defined in accordance with database tables for use in connection with creating protocols in accordance with techniques herein. Element 164 may represent an instrument system having a configuration comprising modules or instruments 1-M. A user may make selections defining an instrument system configuration to include the modules 1-M of 164. For each module of 164, the database may store information regarding which qualification test(s) may be selected when creating a qualification protocol. For example, when module 1 160 is selected as being included in an instrument system configuration, the user may be presented with a menu including the qualification tests 160a. The user may select one or more qualification tests from 160a for inclusion in the qualification protocol being created. In a similar manner, when module M 162 is selected as being included in an instrument system configuration, the user may be presented with a menu including the qualification tests 162a. The user may select one or more qualification tests from 162a for inclusion in the qualification protocol being created. The foregoing may be performed for each module included in an instrument system configuration. Additionally, the database may have defined associations between qualification tests and groupings of multiple modules. In other words, when an instrument system includes a particular combination of two or more modules, the user may also be presented with an option to select from another set of qualification tests associated with testing an aspect of the combination of the two or more modules. For example, an LC instrument system may include the modules of 164 including an injector, pump and detector. For such an LC system configuration the user may be presented with a menu including tests 166 from which the user may select one or more tests for inclusion in the qualification protocol being created. As an example, qualification tests which are associated with, and may vary with, a single module or instrument such as illustrated by 160a, 162a may be IQ tests. Qualification tests which are associated with, and may vary with, a group of modules such as illustrated by 166 may include OQ and/or PQ tests.

As noted above, a UI such as of a qualification protocol editor may be used in connection with creating and storing qualification protocols in accordance with techniques herein. The UI may use information from the database in connection with the foregoing processing to populate and display menu items and to obtain user selections. For example, the UI may use information from the database to populate a UI menu with defined qualification entity categories. A user may make a selection regarding one of the qualification entity categories for which the qualification protocol is being created. When creating qualification protocols for an instrument system as the qualification entity category, the user may be prompted to input additional selections regarding the modules comprising the instrument system configuration for which the protocol is being created. The particular qualification entity categories, modules, and the like, from which the user may select in connection with a particular embodiment may be defined in database structures used in connection with populating the menu from which a user may make selections for protocol creation. Depending on the particular components or modules comprising each instrument system, the user may then select one or more different qualification tests associated with each such instrument system (e.g., combination of multiple components or instruments in a single instrument system) as well as for each component or instrument included in the single instrument system. For example, for an LC instrument system, a user may select from a set of IQ tests for the particular detector of the system and may also select from a set of OQ and/or PQ tests to test the combination of pump, injector and detector comprising the LC instrument system.

For each qualification test, additional information may be obtained from the database and/or via user inputs. Each qualification test may be characterized as either non-analytical or analytical. A manual test is one example of a non-analytical test that may be performed manually such as with the user initiating execution of the test via UI selections and having the user perform other steps manually as may vary with test (e.g., read a measurement, manually confirm or inspect various installation aspects of an instrument related to its installation environment). In contrast, an analytical test may be an automated test that performs an analysis by running the instrument system. For example, a non-analytical test may be a temperature test such as where an LC column may be heated or cooled and the resulting temperature is measured. For an LC instrument system, an example of an analytical test may be injection volume linearity or detector linearity involving operation and coordination of all instruments in the system to obtain analytical test results particular to the instrument system such as regarding the instrument system's performance, accuracy, and the like.

Each test has an associated UI that will be displayed when executing a protocol and performing the test. The database may identify the particular UI template for each test used when the protocol runs. For example, in connection with an analytical test, the displayed UI and associated template may include particular UI features such as a progress bar, particular menus, buttons, and the like, as may be associated with an analytical test. Additional information of the UI template may be populated with other information such as menu options for the particular test.

Figure 5:
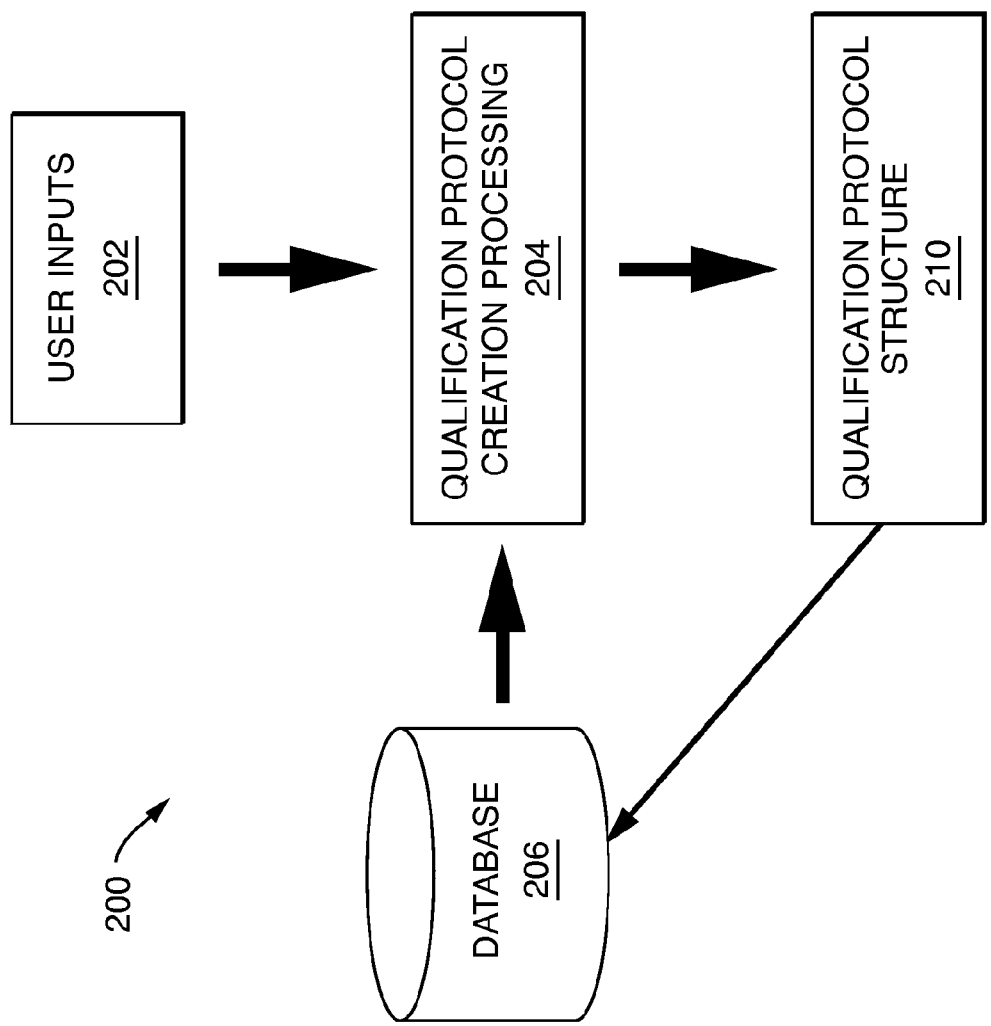
FIGS. 5, 7, and 9 are examples illustrating data flow and components that may be used in an embodiment in accordance with techniques herein for a qualification protocol and associated structure.

Consistent with the above-noted discussion and now referring to FIG. 5, shown is an example illustrating components that may be used in an embodiment in connection with creating a qualification protocol structure or template in accordance with techniques herein. The example 200 includes user inputs 202 which may be input to qualification protocol creation processing 204. Element 204 may be implemented using software include code that is executed in a processor of a computer system. Processing 204 may also use as input information from database 206. The processing 204 may generate a qualification protocol structure 210 based on the user inputs 202 and information input from the database 206. The information from the database 206 may be used in connection with various user interface (UI) displays to obtain user inputs 202. Additionally, information may be extracted from the database 206 based on user selections and such extracted information may be included in the qualification protocol structure or template 210. The generated structure or template 210 may be stored in the database 206.

Figure 6:
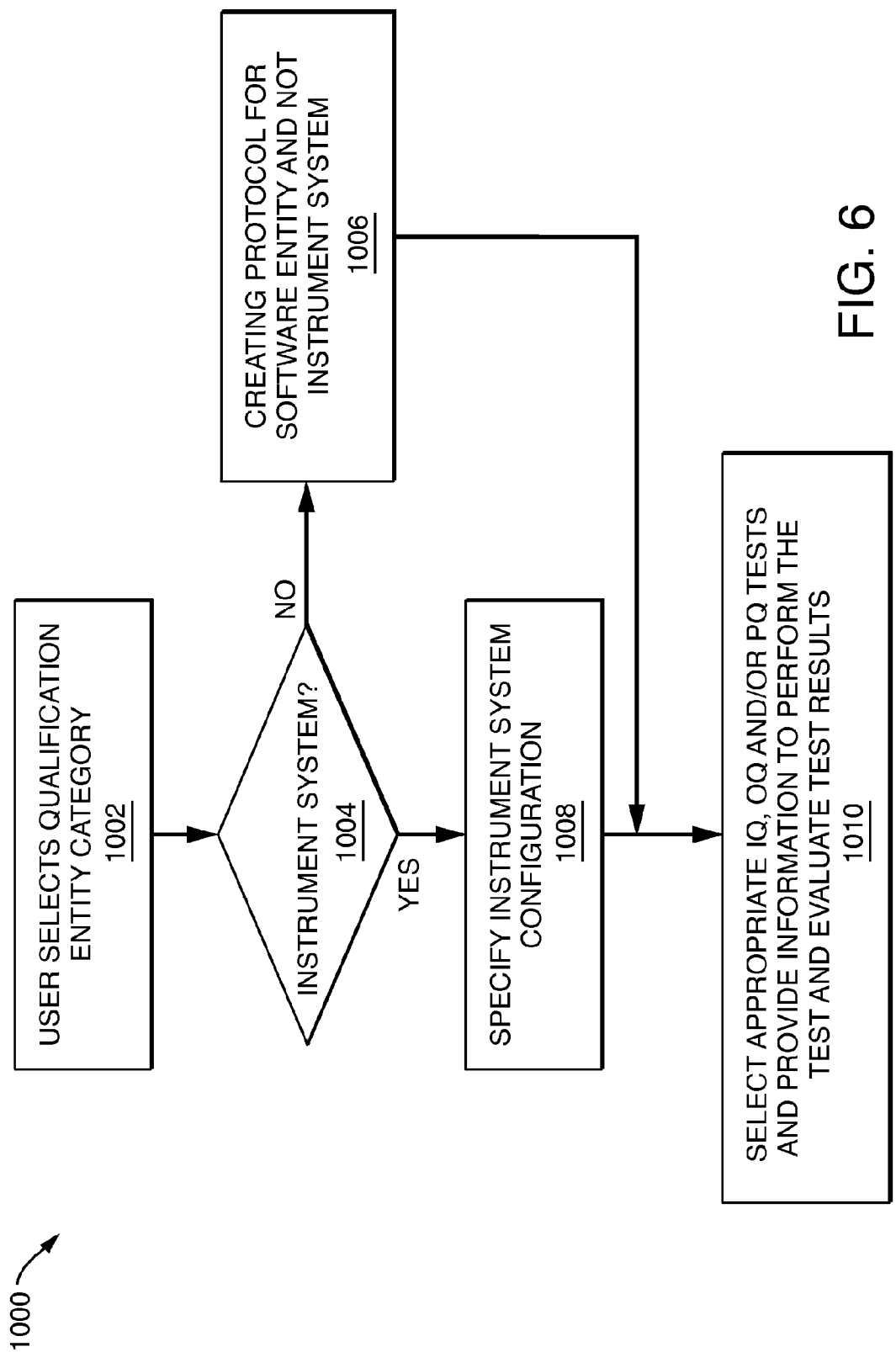
FIGS. 6, 20 and 21 are flowcharts of processing steps that may be performed in an embodiment in accordance with techniques herein.

Referring to FIG. 6, shown is a flowchart of processing as may be performed by a user in connection with techniques herein to create a testing protocol using a UI providing a dialogue, menu selections, and the like, in an embodiment in accordance with techniques herein. At step 1002, the user selects a qualification entity category such as instrument system or software. At step 1004, a determination is made as to whether the selected category is instrument system. If so, control proceeds to step 1008 where the user specifies the instrument system configuration. In step 1010, the user selects one or more appropriate IQ, OQ and/or PQ tests to be included in the protocol. Additionally, the user provides information (along with any other information extracted from the database as described herein) in order to specify information to perform the test and evaluate the test results.

Besides including functionality to create qualification protocols and associated structures, an embodiment may also include functionality to modify and/or delete existing qualification protocols and associated structures or templates.

Figure 7:
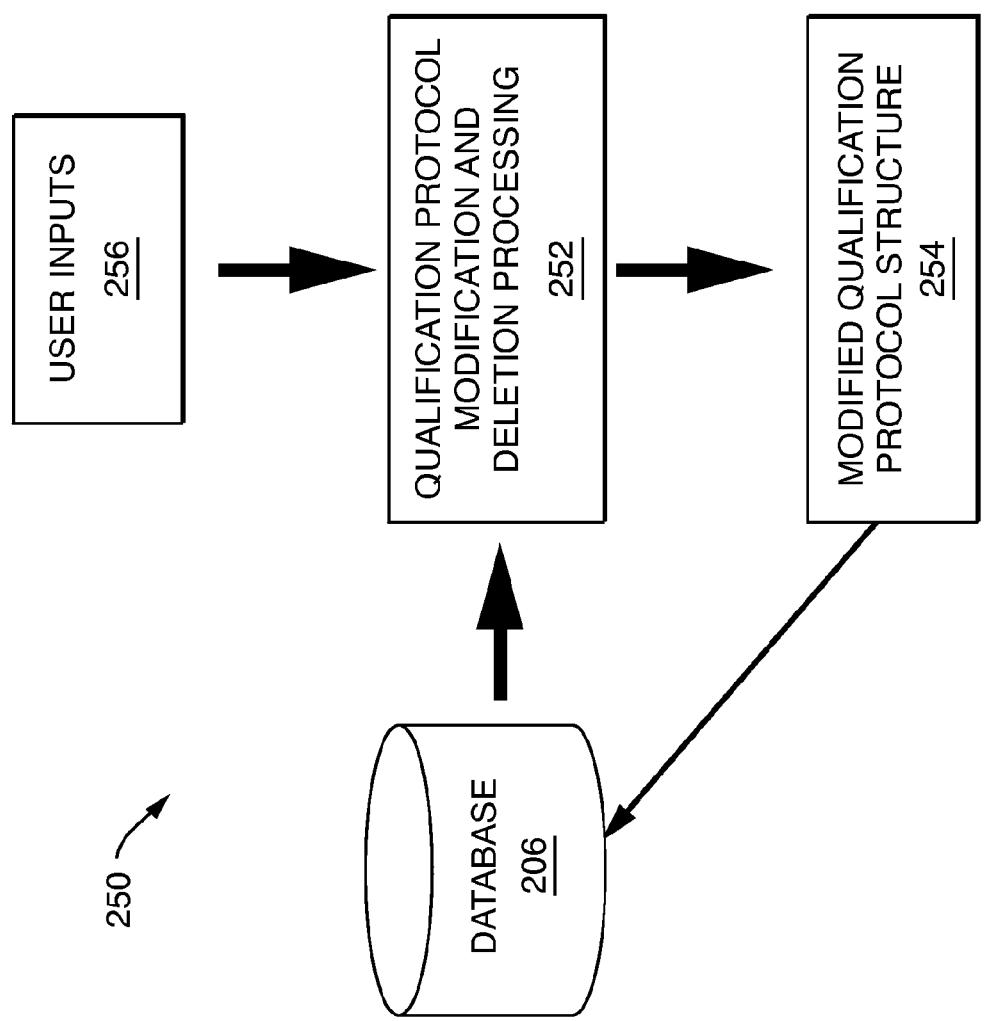

Referring to FIG. 7, shown is an example illustrating components that may be used in an embodiment in connection with modification and/or deletion of qualification protocols and associated structures or templates in accordance with techniques herein. The example 200 includes user inputs 256 which may be input to qualification protocol modification and deletion processing 204. Element 206 may be implemented using software include code that is executed in a processor of a computer system. One of the user inputs 256 may be a selection to perform either modification processing or deletion processing with respect to an existing qualification protocol structure stored in the database 206. In response to a user selection to perform qualification protocol structure modification, processing 252 may include selecting an existing protocol and associated structure for modification from the database 206, modifying the selected protocol and associated structure and generate a modified qualification protocol structure 254, and then storing the modified protocol structure 254 in the database 206. The modified structure 254 may replace the previous version of the structure that existed in the database 206 prior to modification. The processing for protocol modification may vary depending on the particular modification. For example, the modification may include modifying any aspect of the existing protocol and associated structure which dictates subsequent steps performed. For example, for a defined qualification protocol a user may delete a qualification test, may add a qualification test (e.g., which may also trigger additional processing to obtain information regarding the newly selected test), or a user may add, delete or replace a module or instrument in an existing system configuration (e.g., where such adding or replacing may also trigger reselection of appropriate qualification tests, obtaining information for the selected tests, and the like). In response to a user selection to perform qualification protocol deletion, processing 252 may include selecting an existing protocol and associated structure for modification from the database 206 and deleting the selected protocol and associated structure from the database 206.

Figure 8:
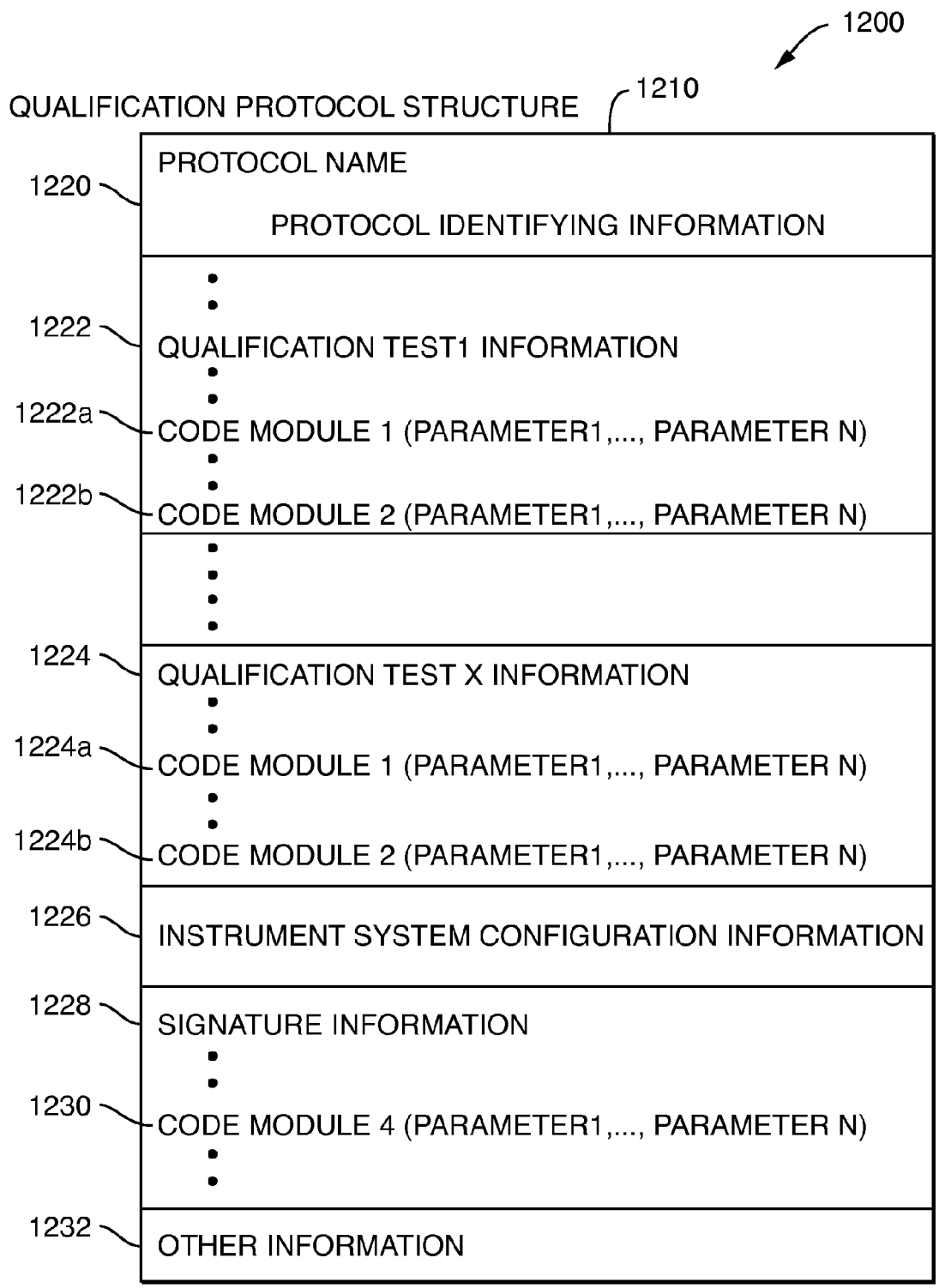
FIGS. 8 and 10-12 are examples illustrating information that may be included in a qualification protocol structure as may be used in an embodiment in accordance with techniques herein.

Referring to FIG. 8, shown is an example representing information that may be included in a qualification protocol structure in an embodiment in accordance with techniques herein. In the example 1200, the structure 1210 may be characterized as a parameterized template of information used for one or more qualification tests of the protocol. As described herein, such information may be used, for example, to execute the qualification tests, evaluate the test result data generated by execution of the tests, generate reports for the qualification tests, and obtain signoff and approval regarding the qualification tests. The information represented in structure 1210 may be organized in any one or more different ways as may vary with embodiment. Generally, the structure 1210 may include information describing and identifying the qualification protocol, identifying the code modules to be invoked and executed to perform the qualification test and generate test results, to perform reporting on the test results, to evaluate the test results, and to obtain the necessary signatures as may be needed to approve the test results. The example 1200 abstractly represents information that may be included in a generated qualification protocol structure in an embodiment in accordance with techniques herein. In one embodiment, the structure may be described using XML. An example of an XML-based schema that may be used for the structure in an embodiment is described elsewhere herein in more detail.

The qualification protocol structure 1210 may include general information about the protocol 1220 such as a protocol name and other identifying information for the protocol defined by the structure 1210. The protocol name may be used to uniquely identify and distinguish this protocol from others that may also be defined. The structure 1210 may include information for one or more qualification tests of the protocol. For example, element 1222 may represent information in the structure 1210 used in connection with a first test, QUALIFICATION TEST 1. For the first test, the structure 1210 may specify one or more code modules 1222a, 1222b to be invoked at a later point in time when executing the represented protocol. For example, element 1222a specifies that code module 1 is invoked with the parameter list having values that may be provided in the structure. In other words, 1222a may be characterized as identifying a code module such as a routine or method that is called and executed at runtime as part of executing the qualification protocol. Similarly, element 1222b specifies that code module 2 is invoked with the parameter list having values that may be provided in the structure and 1222b may be characterized as identifying a code module such as a routine or method that is called and executed at runtime as part of executing the tests of the protocol. Elements 1222a, 1222b may represent code modules invoked, for example, to perform a qualification test generating test results, interpret, filter and evaluate test results, and/or generate a report regarding an executed test. As described in more detail elsewhere herein, a code module performing a qualification test may perform processing, for example, to set and test instrument operating parameters, obtain analytical results from operating an instrument system to perform analysis of a sample, and the like. If the entity being qualified is software, the code module performing a qualification test may perform processing, for example, to obtain results from executing software being qualified, compare the results to expected results (e.g., benchmarks), and the like. In a similar manner as just described for element 1222, element 1224 may represent information in the structure 1210 used in connection with a second test, QUALIFICATION TEST X, of the protocol.

If the qualification protocol is used in connection with an instrument system, such as a scientific instrument system, the structure 1210 may include information 1226 describing the configuration of the system such as, for example, the particular components or modules comprising the instrument system for which the qualification protocol is used to test. The structure 1210 may include signature information 1228 and more generally other information 1232 as may vary with embodiment. Signature information 1228 may include information identifying the code module invoked in order to complete digitally signing the report and/or other documentation for approving test qualification results. For example, signature information 1228 may include 1230 identifying code module 4, such as a routine or method, that is called and executed at runtime as part of executing the tests of the protocol.

Figure 9:
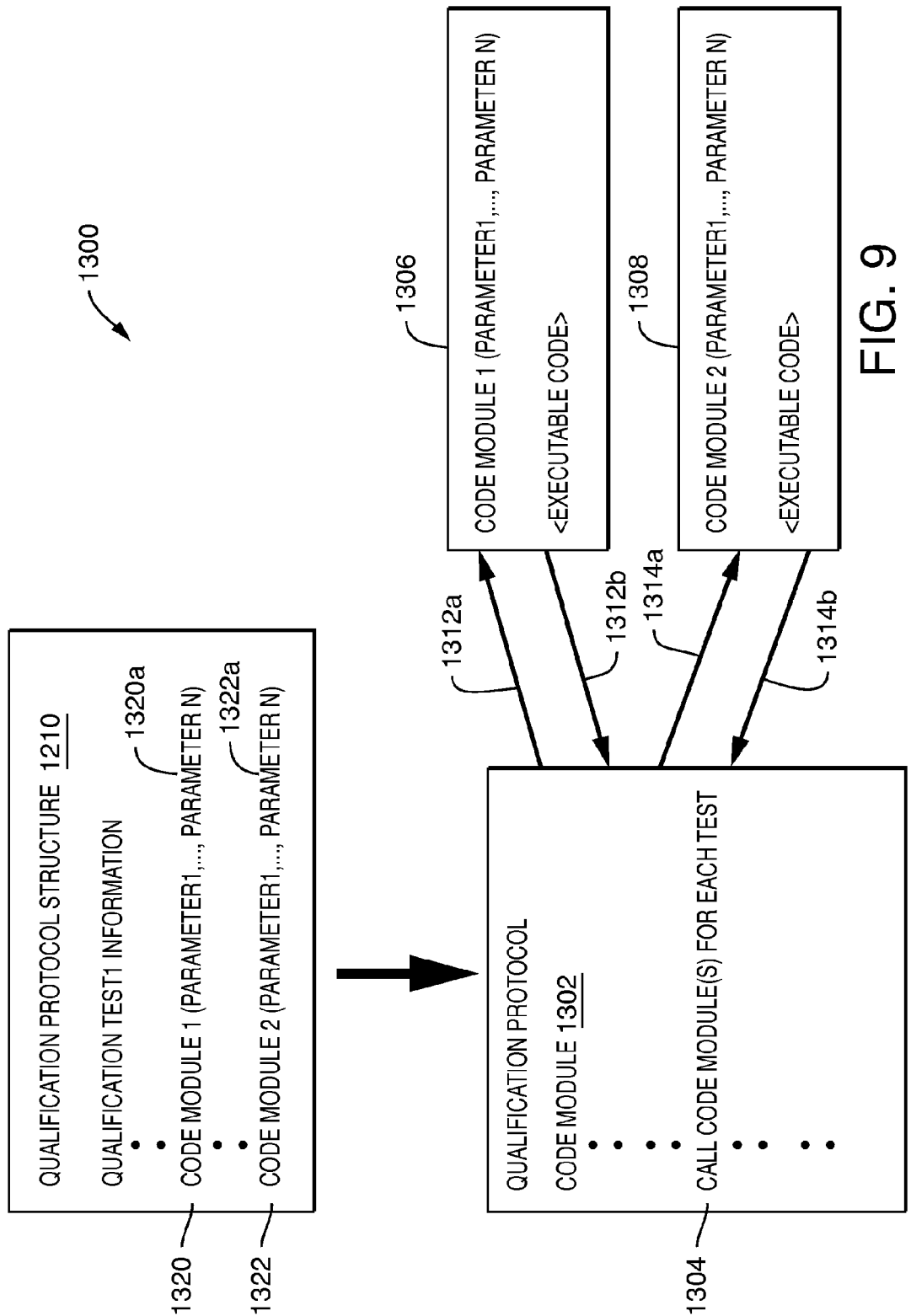

Referring to FIG. 9, shown is an example illustrating how the qualification protocol structure defined for a qualification protocol may be used in connection with executing the tests of the protocol. The example 1300 includes qualification protocol structure 1210 such as described in connection with FIG. 8. The structure 1210 may be generated as described herein, for example, in connection with FIG. 5. Elements 1302, 1306 and 1308 may represent code that is installed and loaded on a computer or other system with a processor executing such code. For example, code represented by 1302, 1306 and 1308 may be installed on a customer's computer system and module 1302 may be invoked by the customer in connection with performing qualification testing for an instrument system or software of the computer system at the customer's site. During execution of module 1302, structure 1210 may be read as an input and interpreted by module 1302. More specifically, the module 1302 may input the structure 1210 and use the information of structure 1210 to drive execution of the qualification tests of the qualification protocol described by 1210. For example, code module 1302 may include instruction to read information 1320 from 1210, transfer runtime control to the identified code module, and provide the identified code module with parameters as may be included in 1320. After the identified code module is executed, runtime control is transferred back to the module 1302. In this manner, the structure 1210 may include information that drives execution of the tests of the protocol. To further illustrate, module 1302 may include instructions 1304 which invoke each of the code modules identified in the structure 1210. During execution of module 1302, data of 1320 is input and processed where such processing include transferring control 1312*a* to code module 1 1306 with parameter information 1320*a*, executing code of 1306, and then transferring control 1312*b* back to module 1302. In a similar manner, code module 2 1308 may be invoked in response to inputting and processing 1322. Module 1308 is invoked 1314*a* with parameter information 1322*a*, code of module 1308 is executed, and then control is transferred 1314*b* back to module 1302.

Figure 10:
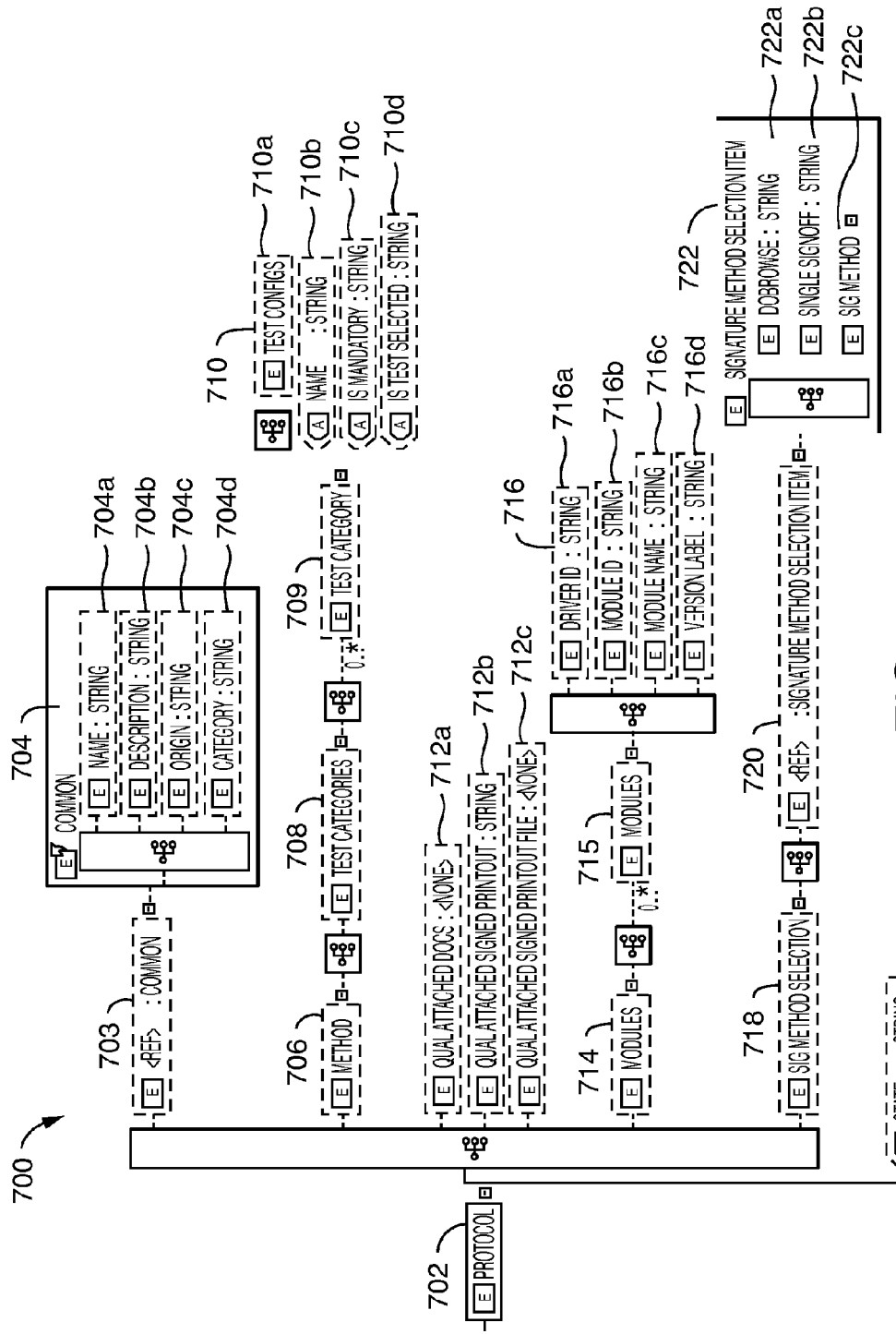

Referring to FIG. 10, shown is an example of information that may be included in a defined schema, such as an XML schema, for each created qualification protocol structure or template. Information represented in the example 700 may be included in an XML generated file that serves as the qualification protocol structure or template described elsewhere herein as a result of protocol creation processing. Each protocol 702 may have a set of common information or attributes 703 specified as indicated in structure 704. For each test qualification protocol, 704 may include a name 704 (e.g., the name uniquely identifying the described protocol to distinguish it from other named protocols), a description 704*b* (e.g., text description of the protocol), an origin 704*c* (e.g., indicating a source, creator, author and/or supplier of the protocol such as a particular vendor of a vendor-supplied protocol), and a category 704*d*. Element 704*d* may be one of the predefined categories of qualification protocol entities for which a protocol may be created. For example, as described elsewhere herein in one embodiment, element 704*d* may be specify an instrument system or software. The user specifies 704*a*-704*c*, such as via a UI, and also may select a category for 704*d* from a menu of predefined categories available in an embodiment.

When 704*d* indicates that this protocol 702 is defined for an instrument system, the instrument system configuration may be specified to include one or more modules 714. Each module is represented by an instance of 715 for which module attributes, or more generally, module-specific information 716 may be specified. In this example, module information 716 may include information represented by elements 716*a*-716*d*. Information 716 may be retrieved from a database of module information for existing modules. As described elsewhere herein, a user may be presented with a list of existing modules (or instruments) from which the user may make one or more selections denoting the selected modules comprising the instrument system for which the protocol is created. Based on the user selections, appropriate module information may be retrieved from the database and included in the generated qualification protocol structure. In this example element 716*a* specifies the identifier of the driver software that may be installed and a system and used in connection with communications between the instrument and other system components such as, for example, to issue commands to set instrument parameters (e.g., temperature, voltage, and the like, as may be appropriate for each module) and to operate the instrument to perform processing in connection with a test (e.g., inject a sample into an LC system). Element 716*c* may be a descriptive string identifier of the module (e.g., vacuum pump). Element 716*b* may specify a particular model of the particular instrument/module (e.g. one of multiple vacuum pump models). Element 716*d* may indicate a version number as related to any of the driver and/or module.

Element 706 identifies one or more methods, or more generally, code modules, that are executed to perform one or more tests. A method 706 may be associated with one or more test categories 708 such as, for example, IQ, OQ and/or PQ. For each test category 709, test information 710 may be specified and may include test configuration information 710*a*, name 710*b* (e.g., description of test as included in the database), is mandatory 710*c* (e.g., boolean value indicating whether the test is required when executing the protocol or may be optionally selected for testing when executing the protocol), and isTestSelected 710*d* (e.g., boolean indicating whether the user has selected this particular test to be included in the protocol).

A user creating a qualification protocol in accordance with techniques herein may specify parameters, such as values, included in 710a affecting how the selected test is to be executed. The information included in 710a may vary with test and module/instrument, and/or instrument system and is described in more detail in connection with FIG. 11. To further illustrate, a single method or code module 706 may perform 4 IQ tests (e.g., IQ specified using 709). Of the 4 IQ tests for which the method includes code, a user may have selected 2 of the 4 IQ tests to be included in a protocol being created. An instance of 710 may be specified for each of the 4 IQ tests and additional information included in 710 may be specified by the user for each of the two tests included in the protocol.

Elements 718, 720 and 722 specify the particular signature or signoff required such as in connection with qualification test results review and approval described elsewhere herein. DoBrowse 722a may be a boolean indicating whether a user is presented with an option to browse for a signature method at runtime when executing the protocol. When 722a is set to true, the user is allowed to browse via menu selection during testing protocol execution to select a signature method. Otherwise, the user may be presented with a default approval/signature option during protocol execution. SingleSignOff 722b may be a boolean indicating whether a single sign off or approval is used in connection with the testing protocol. For example, if 722b is FALSE then an embodiment may implement a multi-level signoff approval in connection with the protocol. In this case, a first level of signature and approval may be associated with a set of IQ tests and another signature associated with a set of OQ/PQ tests included in the protocol. Additionally, a second level of signature and approval may be associated with the entire protocol. This is described elsewhere herein in connection with the exemplary illustrated execution of a qualification test protocol in accordance with techniques herein. Alternatively, if element 722b is true, only the first level or only the second level of signature approval may be included in the protocol, but not both. Element 722c may identify a method, or more generally, a code module, which may be executed at a subsequent point in time when executing the testing protocol and performing the signature approval. Elements 712a-c may collectively represent a set of files (e.g., protocol description, operating procedures, and the like), that may be attached to a protocol and may be used in connection with an execution of the protocol. For example, a document may be attached as documentation for a user who executes the protocol where the user reviews and/or approves test results. Such documentation may provide documentation describing, for example, the test performed, goals of the test, relevance to qualification, aspects being qualified or tested, and the like. Element 724 may be set to one of multiple predefined status values reflecting a current state of the protocol. For example, in one embodiment, element 724 may be set to any of approved, not approved, or rejected. The foregoing status value at a point in time may allow or restrict usage and execution of the protocol. For example, a rejected protocol may not be used to run a qualification. Usage of a protocol having a "not approved" status may be controlled in accordance with a defined policy of a system. For example, some systems may allow limited use and execution of selected protocols which are "not approved". Another system may have a policy which indicates that protocols may be executed unless the protocol has a status of approved.

An embodiment in accordance with techniques herein may utilize digital signatures or electronic signatures in connection with approval and signoff for a protocol (e.g., on the entire protocol at one level and also on individual reports as may be generated in connection with one or more set of test results included in a protocol that may include multiple such reports). One form of electronic signature may prompt a user for an account and password or other authentication information to perform the act of electronically signing the report, protocol, and the like. As described elsewhere herein, a digital signature may also be used in connection with exporting an approved protocol such as when exported from a vendor creating a protocol that is subsequently imported for use at another site or system (e.g., a customer of the vendor). As known in the art, a digital signature may be characterized as an electronic signature that may be used to authenticate the identity of the sender of a message or the signer of a document, such as to ensure that the original content of the message or document that has been sent is unchanged. In connection with techniques herein, a electronic or digital signature may be used to sign a report that is being approved or signed off. A digital signature may be used with such a report, whether encrypted or not, so that a subsequent receiver of the report may be ensured of the signer's identity and that the report has not been modified since approved. To further illustrate as may be performed in one embodiment, software may be used to determine a hash value based on the contents of the report. The hash value may be characterized as a token which is mathematically generated based on the contents. As such, the hash value uniquely represents the content of the report at the time of approval/signature. If the report contents changes, so accordingly will its associated hash value for a given algorithm. A signer or user performing the approval may then use a private key such as one obtained from a public-private key authority to encrypt the hash value. The encrypted hash may then be used as the signer's digital signature of the report. In connection with ensuring the data integrity of the report as approved at a later point in time (e.g., ensuring that the report has not been modified), a hash value for the report (e.g., based on the report contents) may be determined at the later point in time. The public key associated with the signer's private key may be used to decrypt the encrypted hash value. If the decrypted hash value matches the hash value determined at the later point in time, then the validity and integrity of the report and signer have been confirmed.

Figure 11:
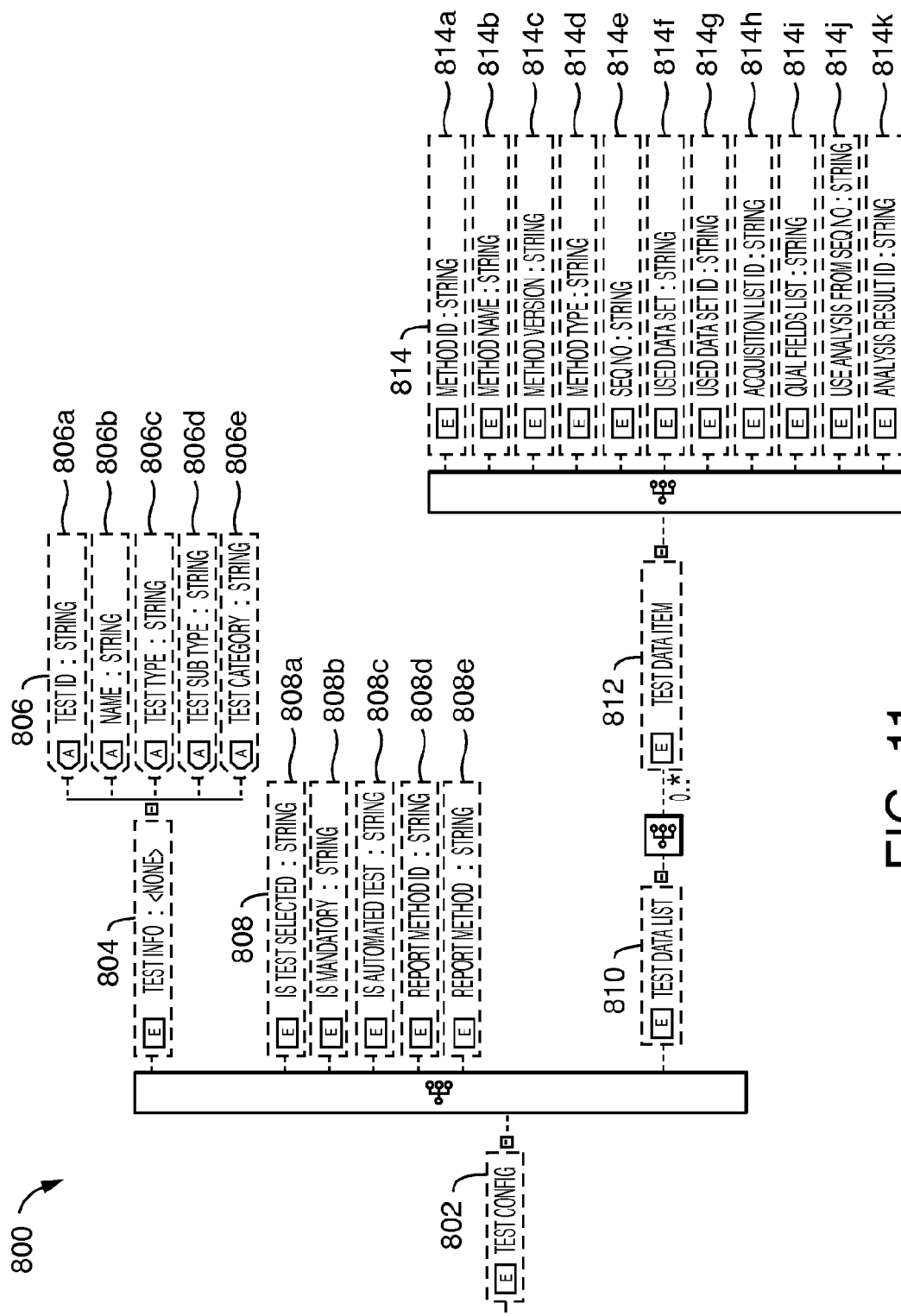

Referring to FIG. 11, shown is an example of test configuration information that may be specified for a test and included in the generated qualification protocol structure or template in an embodiment in accordance with techniques herein. As noted above, the example 800 represents test configuration information 802 for a single test. The set of test info or attributes 806 for a test may include a test identifier (id) 806a (e.g., used to unique identify the test from other possible tests), name 806b (e.g., description of the test) test type 806c and test subtype 806d (e.g., used to identify one or more aspects or modes of test execution including whether the test is automated or non-analytical such as manual), and test category 806e (e.g., one of IQ, OQ or PQ). Information included in 806 may be based on information included in the database for the test. Element 808 may specify a second set of test configuration attributes including isTestSelected 808a (e.g., similar to 710d), isMandatory 808b (e.g., similar to 710c), isAutomatedTest 808c (e.g., boolean indicating whether the user has specified to perform this test manually or automated), reportMethodId 808d and reportMethod 808e (e.g., 808d-e in combination identify the method or code module and the selected report used to perform reporting of the test results). Testdatalist 810 may represent a list of one or more data items 812. Each test data item instance 814 may include items 814a-184d identifying the particular test method (e.g., 814b is a method name used to uniquely identify the method or code module, 814a is an identifier associated with the method named by 814b, 814c may represent the version of the method, and 814d may specify a particular analysis type as may vary with instrument system). It should be noted that 814a-d may be specified for an analytical test and not a non-analytical test. The identified method may be executed, for example, to obtain analytical results through operation of an instrument system. The identified method may also include code that, as described elsewhere herein, evaluates the test results, such as data acquired from the instrument system and determines pass or failure with respect to the test results for the qualification test. Sequence number 814e may specify the order in which the method is executed relative to other methods for the test. For example, a qualification test to perform LC detector linearity may require execution of two methods in sequence and an instance of 814 may be defined for each method. Element 814e indicates the relative order in which such methods are executed for the test. Used data set 814f and used data set identifier 814g may be specify, in combination, an existing data set stored in the database. As one example 814f-g may identify a data set which has been previously acquired using the same instrument system and is stored in the database. The used data set (identified by 814f, g) may serve as an input to the analysis method identified by 814a-814d for further processing. As an example in connection with an MS system, the previously acquired data set identified by 814f-g may be a previously acquired MS spectrum for the instrument which is now being analyzed by a method in connection with calibration.

Analysis result id 814k may be used to identify the data set of the calibration curve data, benchmark threshold values, known "good values" and the like, that may also be stored in the database to which the previously acquired spectrum data is compared. Element 814h may identify experimental parameters used by method when executed in connection with acquiring a new set of analytical instrument data. Element 814h may specify, for example, a number of injections performed, operational parameters values (e.g., temperature, pressure, flow rate, voltage, and the like, as may vary with module and instrument system), sample concentrations, and the like, for use when operating the instrument system and acquire the data set. QualFieldsList 814i includes one or more instance of test qualification field data used to determine a PASS/ERROR (e.g., fail) for each qualification test and is described in more detail in connection with FIG. 12.

UseAnalysisFromSequenceNumber 814j may specify a sequence number associated with a previously executed method for the same test. When 814j is specified, it indicates that the method (identified by 814a-d) uses as an input a resulting data set from previously executed method/sequence number. For example, performing a test may require sequential execution of 3 methods. The output from the second method may serve as an input the third method when 814j has a value of 2 identifying the second executed method. To further illustrate, when running a method to perform an analytical test, the method may have an associated execution mode as described above specified in 806c, 806d. For example, the method may use as input a data set from a previously executed method (e.g. 814j) and/or a data set currently stored in the database. The data set from the database may be a previously acquired data set for the instrument system as described above (e.g., raw previously acquired data set identified by 814f-g) or may be another data set, such as one specifying calibration curve data, benchmark thresholds, and the like, identified using 814k.

Referring to FIG. 8, shown is an example of information that may be specified for an instance of test qualification data (e.g., an instance of information represented by qual field 814i of FIG. 7). As noted above, the example 900 includes information that specifies criterion or criteria to interpret test results and determine whether a status of pass or failure for the qualification test execution that generated the results. One instance of 900 identifies information used to interpret one field in the test results. If test results for test includes 5 fields, for example, that need to be checked, 5 instances of 900 are defined—one for each field to be checked. In one embodiment, elements 904a-d may be used in combination to identify the qualification test results as stored as a field (e.g., a column of data) in a database table of the database where the foregoing field or column may include one or more values. For example, element 904a-d may represent a field such as temperature in an existing database table where the field or column of the table includes multiple numeric values (e.g., that are test results of analysis performed by a method).

FieldCategoryId 904e may be one of a number of predefined testing validation categories affecting how the test results are processed and evaluated. In one embodiment, element 904e may specify SUMMARY (e.g., indicating a summary operation performed on the value(s) included in the fields identified by 904-d described in more detail below), SINGLE, CHANNEL VALUE or CALIBRATION. When SINGLE is specified in 904e the test results are searched for the field specified through the fielded in 904b for each component and perform validation to ensure that the single value for each component is between the range represented by 904j, k, described below.

When CHANNELVALUE is specified in 904e the test results are searched for the field specified using 904b with respect to the combination of each component and the specified channel having a value identified in 'Identification value' 904o (described below). The processing includes performing validation for values in the field to ensure that each such value for each component is between the range represented by 904j, k, described below. The particular meaning imparted to a channel value may vary with entity, such as instrument system or software, being qualified. For example, if the instrument system being qualified is an MS system, CHANNELVALUE may be specified in 904e to represent a particular mass or m/z value. To further illustrate, if the analysis method generates test results for many different mass or m/z values and we are only interested in a particular m/z or mass value, the particular mass or m/z value may be specified using 'Identification value' 904o (described below) and in this case only the test results associated with this identified value in 904o will be validated. Furthermore, summary calculations may be performed on this channel if a summary calculation operator is specified in 904f. Summary calculations can be Maximum (calculating the maximum of the field values for the specified channel), Minimum (similar as above), Mean (the average of the field values for the specified channel), SD (standard deviation), % RSD (relative standard deviation). As a further usage in one embodiment, for example, when used in qualifying an LC detector component of an LC system, CHANNEL VALUE may be specified as a type in 904e in order to calculate a maximum response (e.g., lambda max) for a range of wavelengths for channels. In this case, the summary field 904f specifies a value of "maximum".

When CALIBRATION is specified in 904*e* the test results are searched for the calibration specific fields specified through the field in 904*b* for each component and perform validation to ensure that the single value for each component is between the range represented by 904*j, k*, described below.

Elements 904*f-g* specify a type of summary operation, if any, performed on the value(s) included in the field identified by 904*a-d*. For example, elements 904*a-d* may identify a temperature field in the database table including 5 values. The operation specified by 904*f, g* may specify an average summary operation is to be performed on the foregoing 5 values, a count summary operation indicating to count or quantify the number of values for the field identified by 904*a-d*, standard deviation, variance, and the like, as may be represented by a summary operation encoding using 904*f-g*.

Component name 904*h* may be used as a filter to only examine test result data generated by a single component (e.g. instrument or module) of an instrument system. Value 904*i* specifies an absolute value to which a single test value is compared. ErrorMinLimit 904*j* specifies a lower limit or threshold value. ErrorMaxLimit 904*k* specifies an upper maximum limit or threshold value.

Specification 904*l* is user specified descriptor string description to be included in the report. Result 904*m* may specify the possible test result indicators such as pass or fail. IsMainResult 904*n* is a boolean indicating that specifies whether the result associated with this particular qualField 902 instance for a set of test results indicates the main or primary result. For example, an embodiment may provide for specifying multiple instances of qualField for a single set of test results thereby providing multiple results 904*m*. Element 904*n* may be true to indicate which instance of result 904*m* is the main or primary result. Such information may be included in the report. IdentificationValue 904*o* specifies an expression, such as a regular expression, used to filter results. For example, you may only want to examine test results identified by 904*a-d* over a certain value, such as intensities over a certain amount and a regular expression may be specified using 904 to filter out any value not meeting such criteria. Regular expressions are known in the art and may be characterized as a string used to describe or match a set of strings meeting certain criteria. The particular syntax used to specify the regular expression may vary with embodiment.

As an example, consider elements 904*f-g* that specify an "average" SUMMARY operation as above performed on the value(s) included in the field identified by 904*a-d*. Elements 904*a-d* may identify a temperature field in the database table including 5 values. The operation specified by 904*f, g* may specify an average summary operation is to be performed on the foregoing 5 values. Field 904*i* may be specified to provide a value and indicate to evaluate whether the foregoing average is equal to 904*i*. If not, the test result 904*m* may indicate FAILURE or ERROR. As an alternative, values may be specified in fields 904*j, k*. In this case, a range check is made of the foregoing average to ensure it is between the range of values having a lower limit of 904*j* and an upper limit of 904*k*.

As another example, consider a single test which includes generating a set of analytical data and then analyzing the generated data against a set of benchmark data to ensure that the difference between the two is not more than a threshold amount. In this case, a first method may be executed to generate the analytical data and a second method may be used to perform a comparison and output test result data identifying a difference between corresponding values in the analytical data set and benchmark data. Element 900 may used to evaluate the set of differences to ensure that no single difference value is outside of a specified range represented by 904*j-k*. The named field containing the differences may be specified using 904*a-d*, or more specifically 904*b*. Field 904*o* may also be used to further filter the field identified A value of INDIVIDUAL may be specified in 904*e* in order to filter values in the field specified by 904*b*. Using the foregoing information included in an instance of 900, a test result of PASS is specified if all the differences are within the range indicated by 904*j-k*. Otherwise, the test result is FAIL or ERROR.

The criteria used to interpret and evaluate the test results as included in 900 may be specified by the user using a UI to create or modify a qualification protocol, for example, by selecting and inputting values for appropriate database fields, input validation values and limits (e.g., values for 904*i*-904*k*), and the like.

Figure 12:
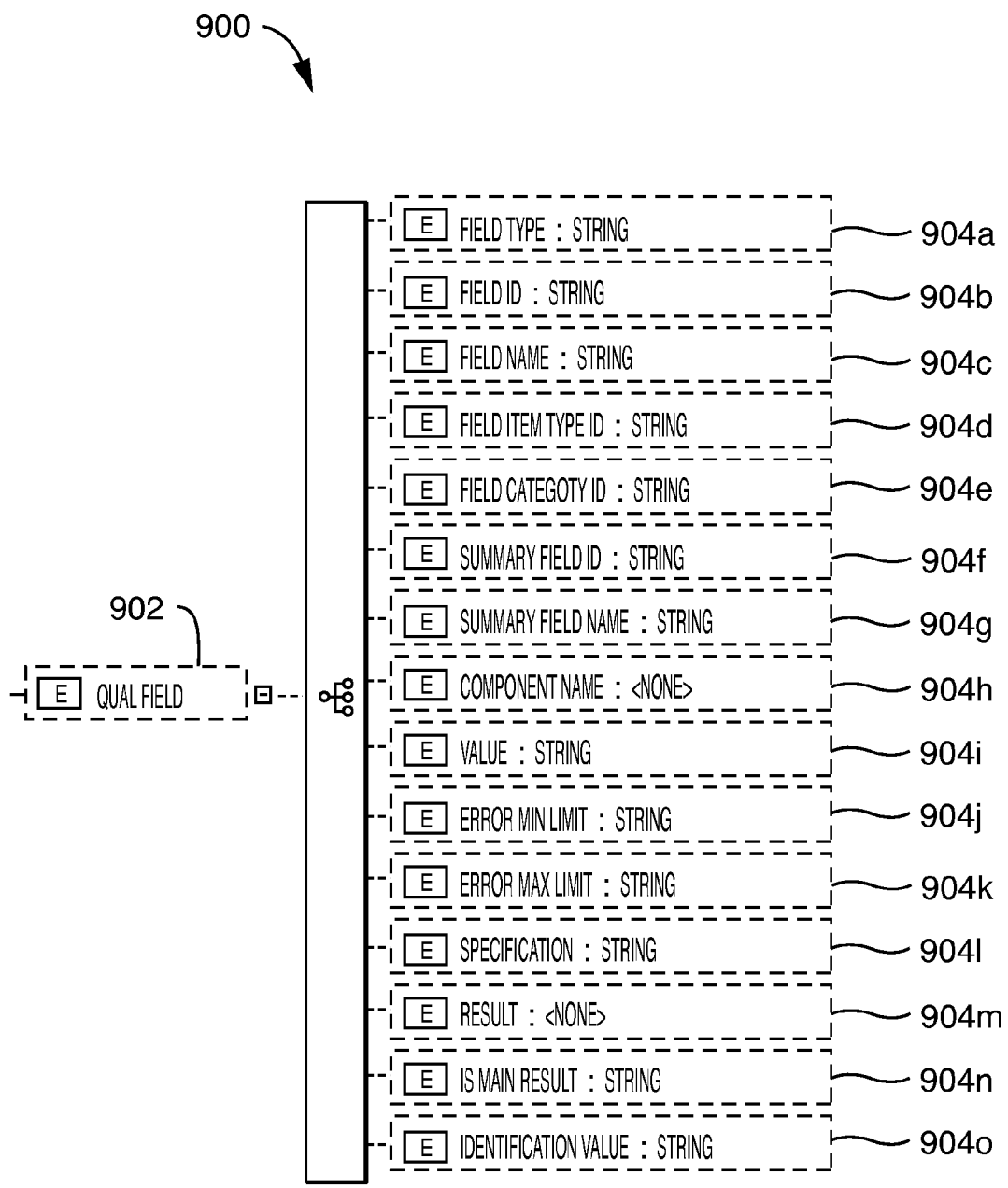

It should noted that FIG. 12 describes one particular way in which an embodiment in accordance with techniques herein may parameterize and encode information used to interpret and evaluate test result data in accordance with techniques herein. As will be appreciated by those of ordinary skill in the art, many other suitable variations are possible and may be specified in the qualification structure. More generally, what will now be described below is the runtime processing that may be performed in an embodiment in accordance with techniques herein using the protocol structure described herein including that as described in connection with FIG. 12, and more generally, as may also be performed in other embodiments using variations of that described in connection with FIG. 12.

Figure 13:
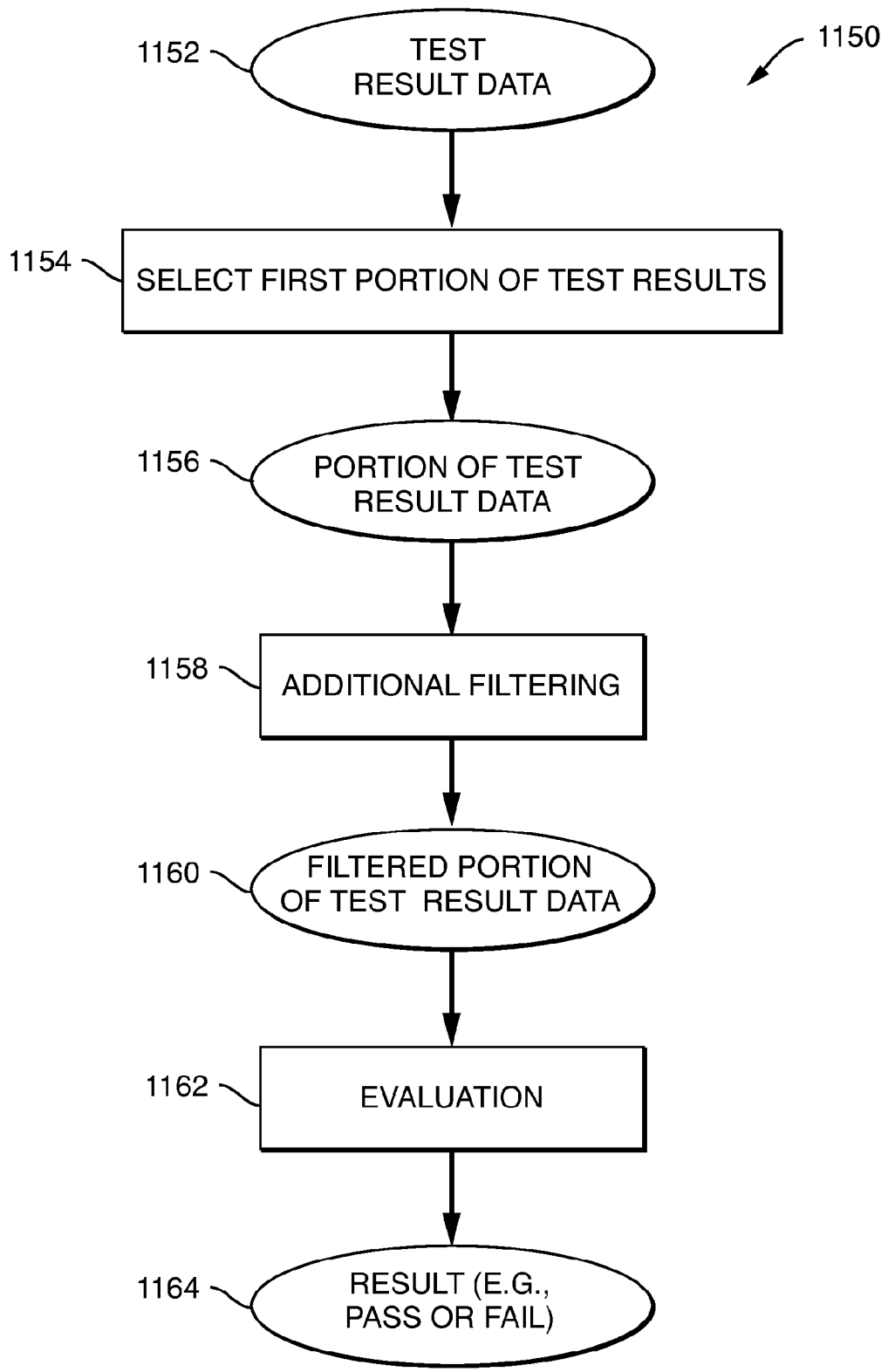
FIG. 13 is an example illustrating processing that may be performed in connection with evaluating test results in an embodiment in accordance with techniques herein.

Referring to FIG. 13, shown is an example illustrating a data flow in connection with processing test result data as may be performed in an embodiment in accordance with techniques herein. As described elsewhere herein, the test result data 1152 may be produced as a result of performing a qualification test included in a protocol. The data 1152 may be processed in step 1154 to select and output a portion 1156 of the original test result data 1152. Step 1154 may be performed by code, such as a selected method, which executes and uses the information such as included in items 904*a-d* of FIG. 12 to select data of a particular field. The portion 1156 may be additionally filtered in step 1158 to further reduce the data to be evaluated to determine whether the qualification test has executed successfully or not. Step 1158 may be performed by code which executes and uses the information such as included in items 904*o* and 904*h* of FIG. 12. An output of step 1158 may be a filtered portion of the test result data 1160. The filtered portion 1160 may then be evaluated in step 1162 to determine a result 1164 such as pass or failure status. Step 1162 may be performed by code which executes and uses the information such as included in items 904*e-g* and 904*i-k* of FIG. 12.

In connection with an entity being qualified that is categorized as software, it will be appreciated by those of ordinary skill in the art that some portions of the schema and test protocol structure such as described herein in FIGS. 10-13 may not be utilized since such portions may not be applicable for use with software and are only relevant for use with other entities such as instrument systems. Alternatively, depending on the particular embodiment in accordance with techniques herein, the elements of the qualification structure may be relevant and have varying meaning and association that vary the qualification entity category. For example, with reference to FIG. 9, elements 714, 715 and 716 may have one meaning and association in connection with software and another different meaning and association in connection with an instrument system.

As described above, creating a qualification protocol in accordance with techniques herein results in generation of a qualification protocol structure or template which identifies the code to be executed, the input parameters, and how to interpret the test results. Prior to finalizing a qualification protocol, processing may be performed to initially create the protocol and also perform one or more subsequent modifications to the protocol. At some point, the protocol may be finalized and approved (e.g., such as with electronic and/or digital signature(s) as described elsewhere herein). The approved qualification protocol having the associated qualification protocol structure may then be exported in a package form which can be transported to the customer or other site. In other words, the protocol may be approved using digital and/or electronic signatures. Additionally, once the protocol is finally approved such as by a vendor completing the qualification protocol, a further level of digital signature(s) may be used as part of processing to export the approved protocol for use in other systems. For example, the approved protocol structure may be encrypted (e.g., optional and varies with embodiment) and digitally signed. The qualification protocol structure may be exported as a signed electronic package from an existing database for use at another system and site. In this manner, an approved protocol may be produced by a vendor or other knowledgeable party and provided to a customer. The customer may import the qualification protocol structure by downloading the signed electronic package including the protocol structure to the customer's site for use in performing qualification testing. For example, the protocol structure may identify code modules, such as methods, included in an installation of software on a customer's computer system. The customer may have installed software (e.g., such as modules 1302, 1306 and 1308 of FIG. 9) which is executed using the parameters and other testing information included in the qualification structure as generated by the vendor or other third party providing the protocol structure. In this manner, the vendor or third party (who may be more knowledgeable than the customer in connection with specifying information used in connection with testing protocols in accordance with different standards, regulations, recommended manufacturer and vendor guidelines, and the like) may generate and distribute an approved qualification protocol structure which may then be used by the customer.

An embodiment may utilize any suitable technique known in the art to protect and verify the data integrity of the qualification protocol structures. For example, the exported qualification protocol structure may be encrypted, digitally signed, and the like, as described elsewhere herein. When the exported qualification protocol structure is used by a customer to perform qualification testing or when imported into the customer's database, processing may be performed to verify or validate integrity of the qualification protocol structure used to ensure the data integrity and authenticity of the structure and thus the defined qualification protocol associated with the structure.

In one application, the qualification protocol structure may be bundled with one or more other software modules. For example, when providing a new instrument driver (e.g., new driver or later version of an existing driver as may be installed on a module of an instrument system) or, more generally, any other new or updated software to be installed on a customer site, the instrument driver or other software may be bundled with a qualification protocol structure including any needed updates to perform the qualification testing using the new driver or other new software. In this manner, any software updates to be installed on the customer site may also be bundled with qualification protocol structures defining qualification testing protocols to qualify the new software updates. For example, the qualification protocol structure provided with a new version of an instrument driver may include the necessary information to perform additional appropriate IQ, OQ and/or PQ testing for the new driver. It should be noted that a driver, such as an instrument driver described elsewhere herein, may be used in connection with device communications between the device and other components, such as between instruments in the same instrument system as well as, for example, from a computer system to an instrument system. The techniques herein may be used to provide and generate an updated or new qualification protocol structure including information needed to identify and run one or more qualification tests for a particular entity (e.g., instrument and/or instrument system) being qualified such as for the new driver. For each test, any necessary parameters are provided or specified using the structure. Each test can be non-analytical or analytical for instrument systems. For analytical tests, the structure identifies the conditions of the experiment using parameters. The structure provides a way to interpret and evaluate the test results. The protocol structure may include information identifying the particular signature or approval method and reporting method. As described herein, the protocol structure may be interpreted by code at runtime to execute tests of the qualification protocol and evaluate and report on test results.

What will now be described are screenshots that may be displayed in connection with a UI when executing a selected qualification test protocol using the techniques herein such as part of a qualification execution wizard. FIGS. 14-19 illustrate steps as may be performed as part of executing a selected qualification test protocol.

Figure 14:
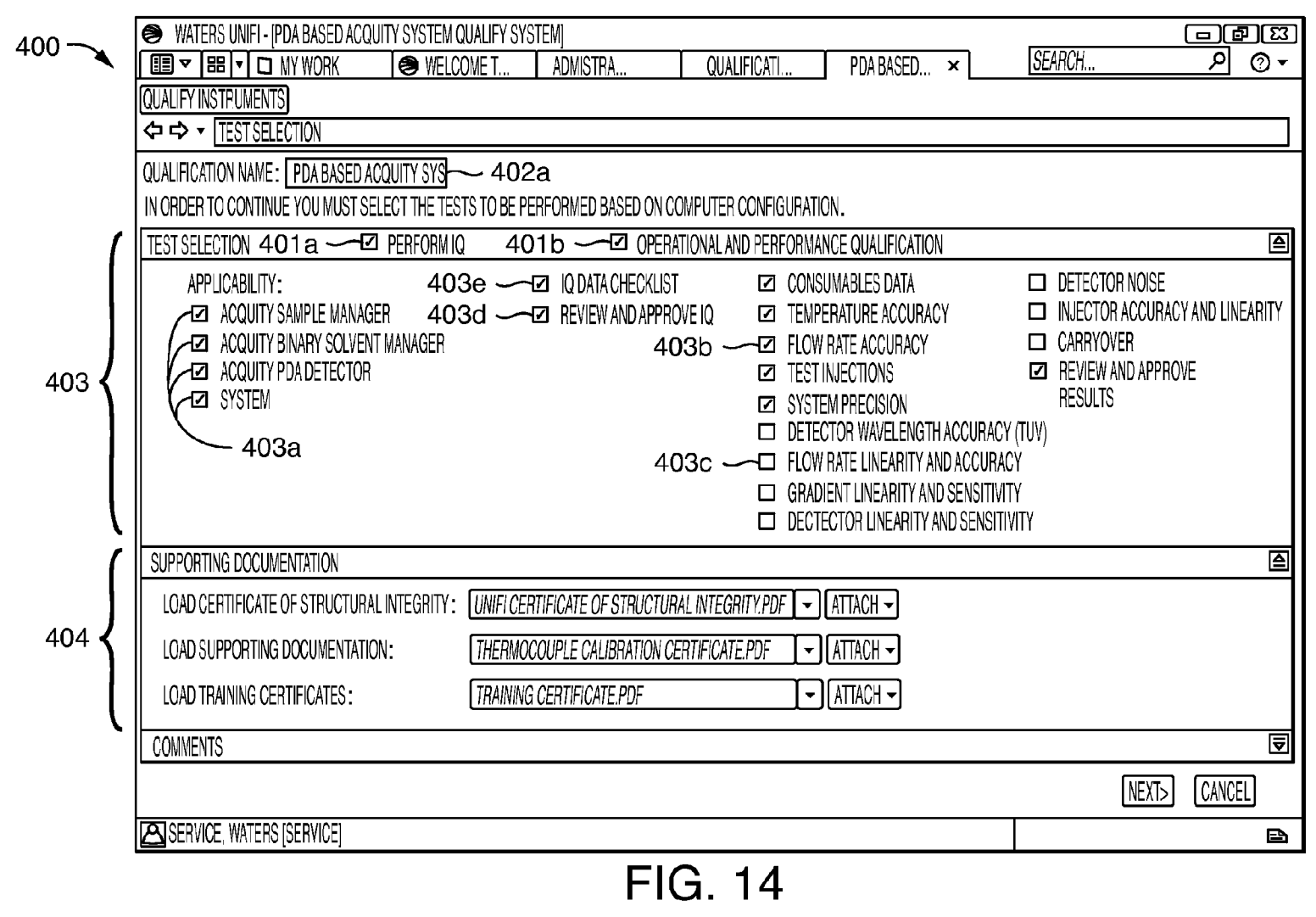

Referring to FIG. 14, shown is an example of a first UI display when executing the selected qualification test protocol. The example 400 illustrates that a test protocol having the name in 402*a* has been selected from execution. In one embodiment, the user may have the option of selecting to execute/not execute tests included in the protocol (e.g., reflecting setting of 710*c* of FIG. 10). Similarly, certain tests may not be optional depending on how the test protocol has been defined. Selections affecting the tests of the protocol of 402*a* which are executed may be made in area 403. For example, IQ and OQ/PQ tests have been included in the selected test protocol and, respectively, selection of 401*a* and/or 401*b* may be used to indicate which general area(s) of tests are desired. In area 403, a user may select which one or more modules or instruments of the system are to be tested (e.g., element 403*a* indicates that testing for the LC detector along with the pump and injector is to be performed, as well as instrument system level testing based on a combination of the system's modules/instruments). In area 403, the user may also select which optional tests (based on 401*a*, 401*b*) are to be performed (e.g., element 403*b* is an optional test for flow rate accuracy which has been selected; element 403*c* is an optional test for flow rate linearity and accuracy which has not been selected). It should be noted that element 403*d* (regarding review and approval for IQ testing) is checked indicating it is to be performed as part of the protocol but is required and may not optionally be deselected/omitted. Element 404 indicates that the user executing the tests has provided electronically necessary certifications as supporting documentation representing that the user has had the proper training to perform qualification in connection with the testing protocol.

FIGS. 15-19 described in following paragraphs illustrate some UIs that may be displayed in connection with executing tests based on selections illustrated in connection with FIG. 14.

Figure 15:
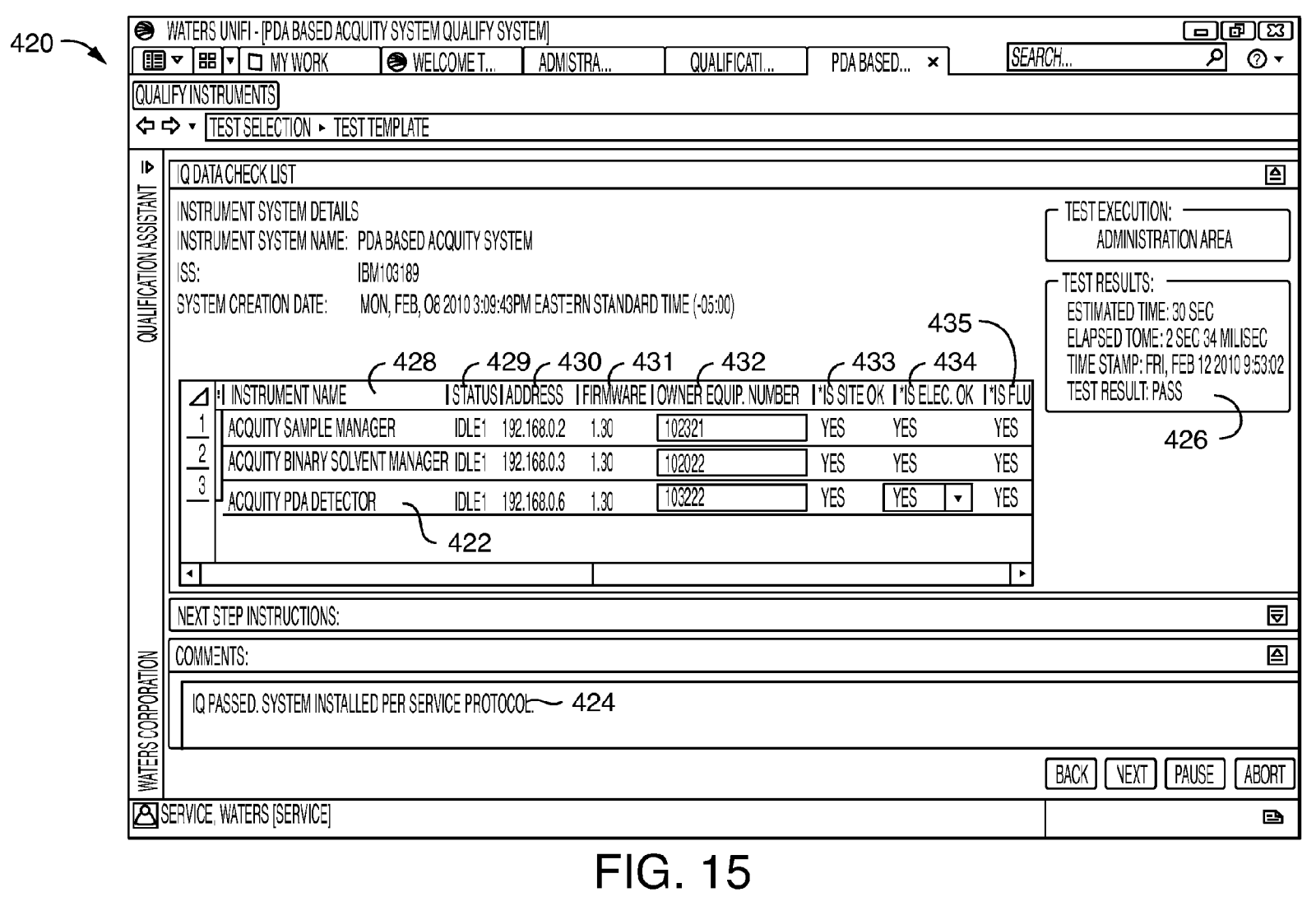

Referring to FIG. 15, shown is an example of a second UI that may be displayed when executing the selected qualification test protocol from the example 400. The example 420 illustrates information in connection with the IQ data checklist 403e from FIG. 14. Information of elements 428, 429, 430, 431 and 432 may be automatically obtained from existing stored information regarding each instrument/component for which the user is manually performing IQ testing. The IQ is non-analytical and manual in that the user examines various installation aspects of the instruments and enters selections in connection with elements 433, 434 and 435 for each instrument. Such IQ testing may be characterized as confirmation, for example, regarding proper electrical connections 434 and fluid connections 435 for the instruments. Although not illustrated, other examples of manual, non-analytical IQ tests may include requiring the user to confirm/verify that the automatically read device address in 430 is correct or that field 430 displays some valid IP address for each instrument. Element 422 may be selected as the current instrument/component for which the user is manually performing IQ testing and entering information in 433, 434, 435, and other columns (not displayed) for the selected instrument 422. Area 426 may display IQ test result information and associated comments may be included in 424.

As described elsewhere herein, each test may be analytical or non-analytical in one embodiment and the IQ testing as illustrated in connection with FIG. 15 is one example of a non-analytical manual test. Other non-analytical tests are illustrated in connection with testing step 2.2, 2.3, and 2.4 such as illustrated in connection with FIGS. 17, 18 and 19.

Figure 16:
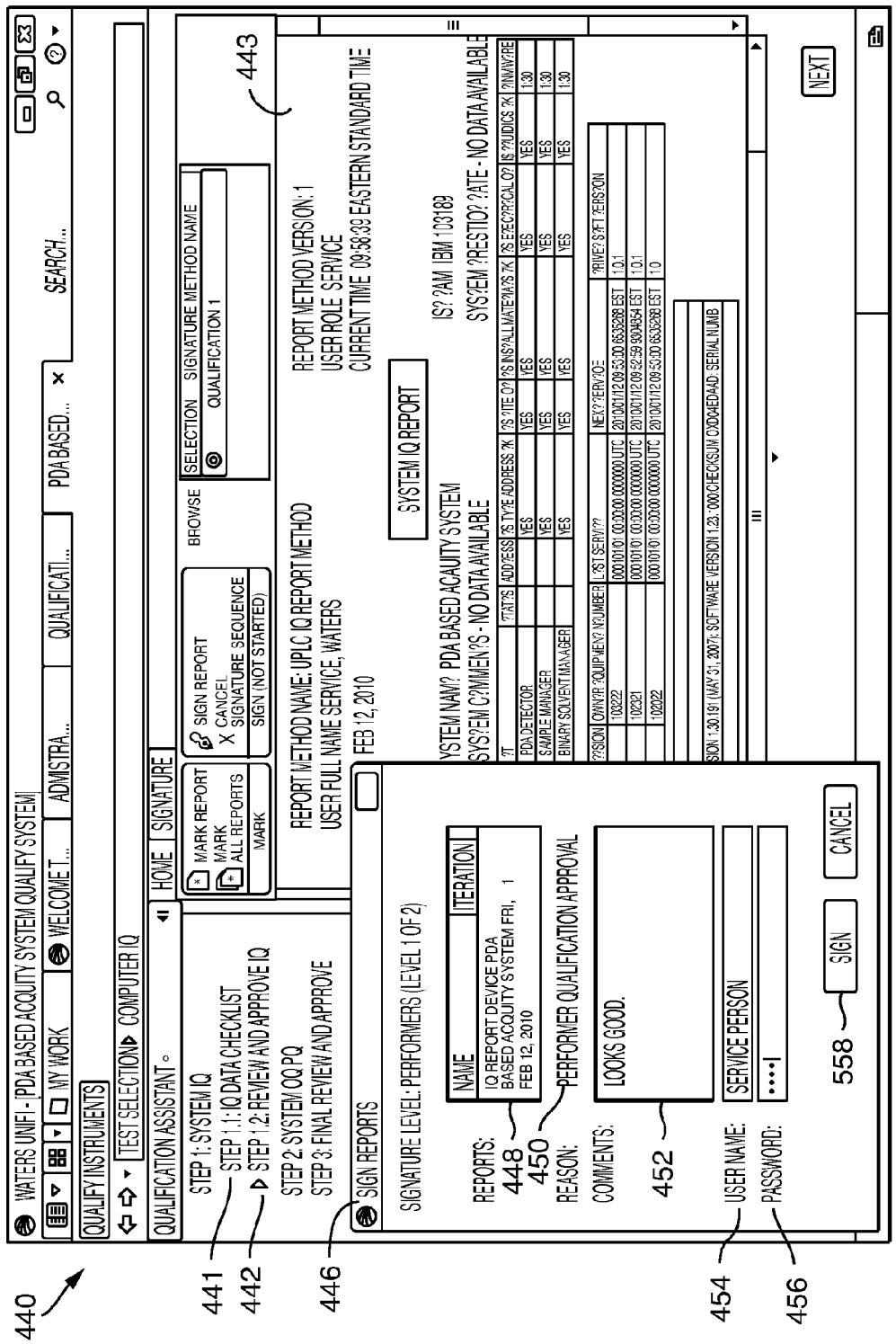

Referring to FIG. 16, after the IQ tests have been completed, the example 440 illustrates a third UI that may be displayed. Element 442 indicates the current step of the test protocol currently being executed which is the review and approval of the IQ test results. It should be noted that element 441 is the step 1.1 corresponding to processing previously performed as described above in connection with FIG. 14. Element 446 illustrates information that may be included as part of electronically reviewing and approving the IQ report 443. Element 448 indicates the name associated with the IQ report being approved. Element 450 indicates that the user performing the qualification is the one reviewing, signing and approving the IQ report 448. Element 452 are any optional comments of the user signing the report. Element 454 indicates the account name and password 456 associated with the user signing the report. Element 558 may be selected once all information in 446 has been entered to submit such information as the electronic signature indicating review and approval of the IQ report 448.

Figure 17:
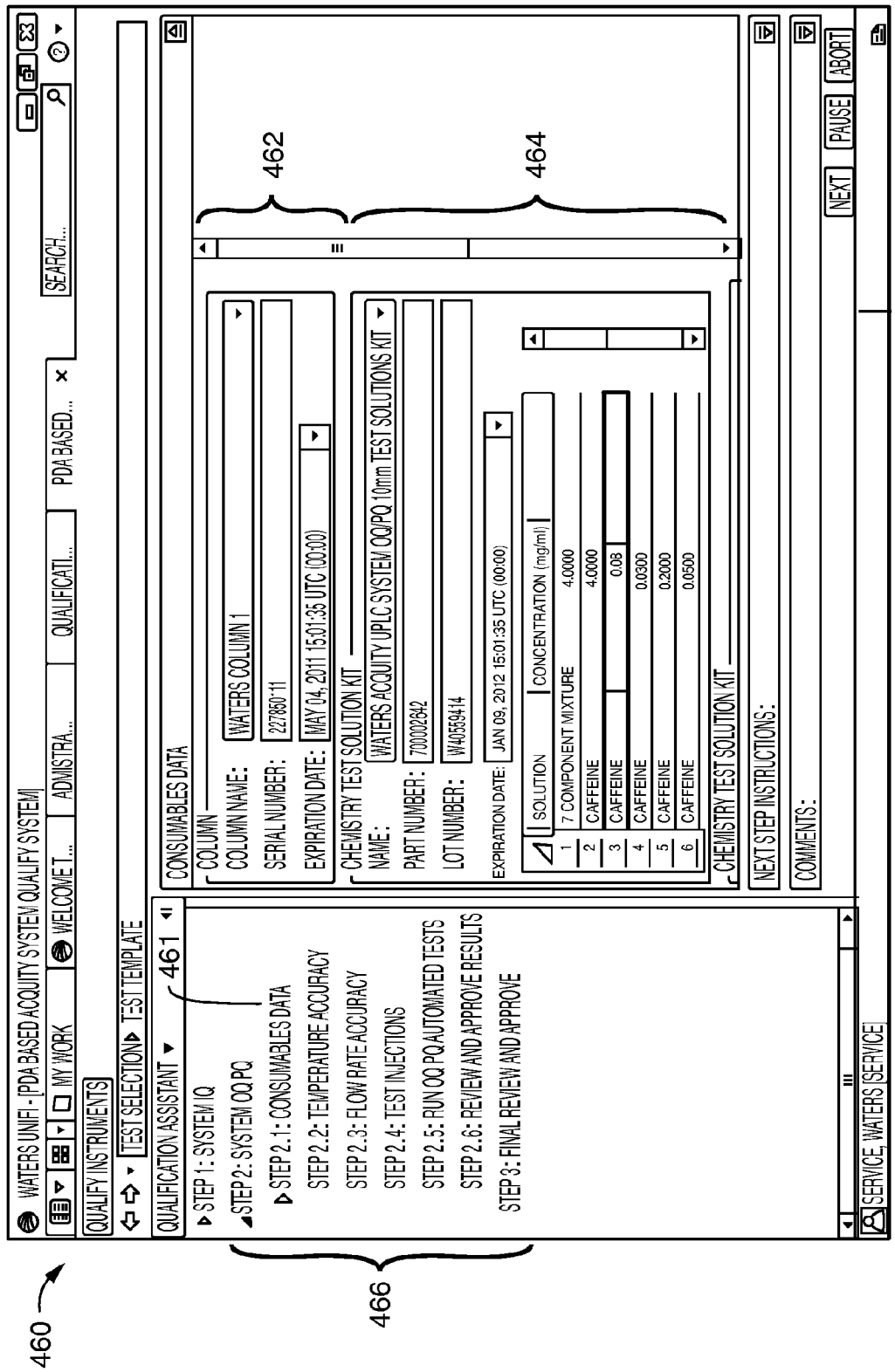

Once the IQ tests have been executed (e.g., FIG. 14) and approved (e.g., FIG. 15), system OQ/PQ tests may be executed with reference to FIG. 17. Element 466 indicates the substeps comprising the system OQ/PQ testing of which the first step 2.1 (461) is represented in the example 460. Area 462 displays information regarding the LC column that may be selected by the user in connection with OQ/PQ tests to be performed. Area 464 displays information regarding the solutions that may be selected by the user in connection with the OQ/PQ tests to be performed.

Figure 18:
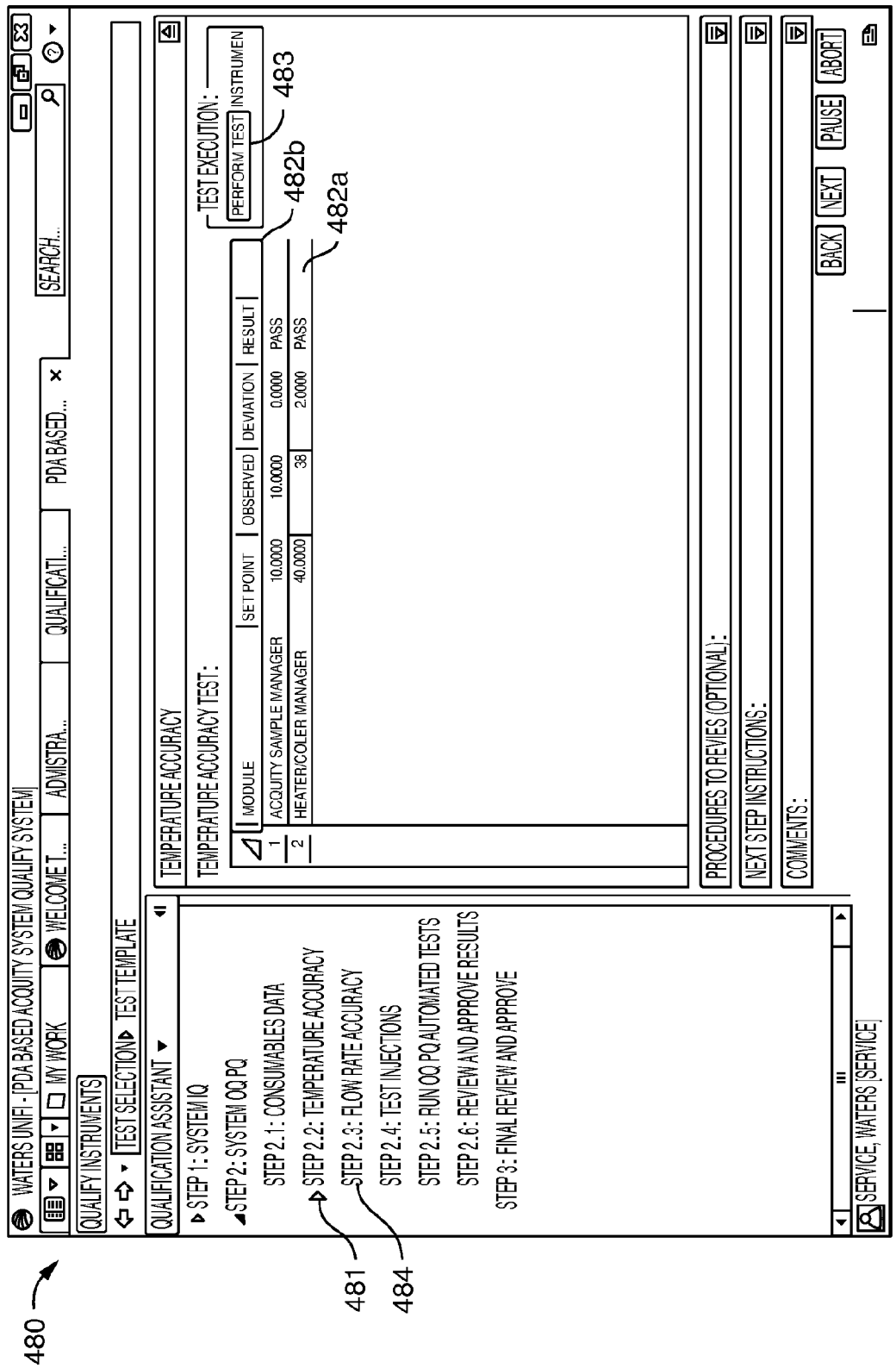
Figure 19:
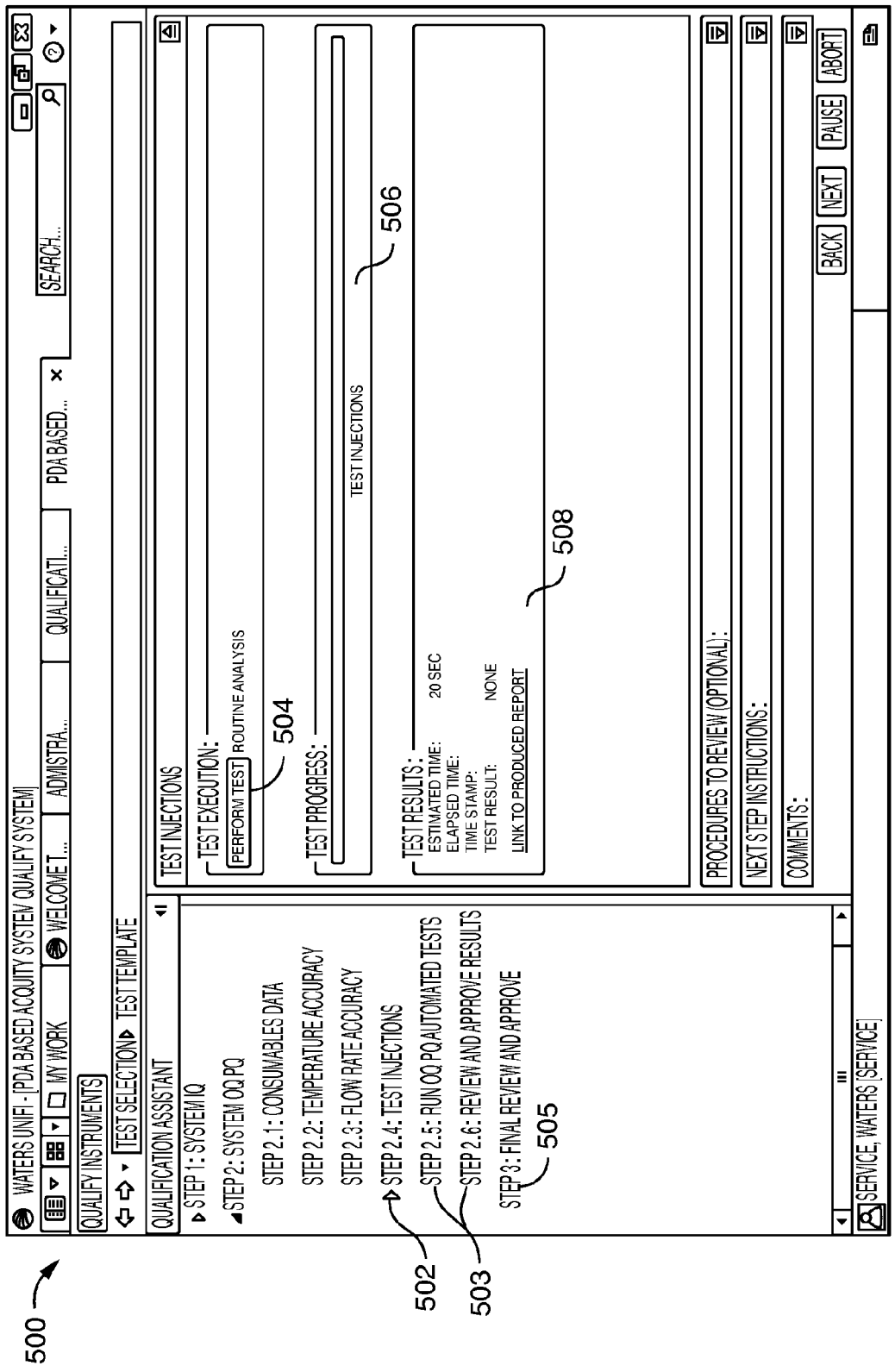

Referring to FIG. 18, shown is an example of a next UI that may be displayed in connection with performing OQ/PQ testing for temperature accuracy 481. The temperature accuracy may be performed for both the modules/instruments 482a, 482b. Element 483 may be selected to perform the temperature accuracy test which, in this example, has been passed by both instruments 482a, 482b. Although not illustrated, another UI may be displayed in connection with performing flow rate accuracy testing 484 prior to displaying the next UI 500 of FIG. 19 in connection with performing test injections. In the example 500, the test injections may be initiated by selecting 504. Area 506 may display the progress of the test injection qualification test. In this example, the test injections are in progress as indicated by area 508. Once the test injection qualification tests 502 have been completed, additional screenshots may be displayed in connection with performing testing for steps 2.5 and 2.6 as represented by element 503. It should be noted that the signing and approval of step 2.6 and associated UI display may be similar to that as illustrated in connection with FIG. 16 for IQ testing. Once all IQ and OQ/PQ tests have been completed, a final review and approval 505 may be performed indicating a second level of review and approval of the qualification testing overall. Step 505 may require different and/or additional signatures than those associated with approval in step 1.2 for IQ testing approval (e.g., FIG. 16) or step 2.6 for OQ/PQ testing.

Figure 20:
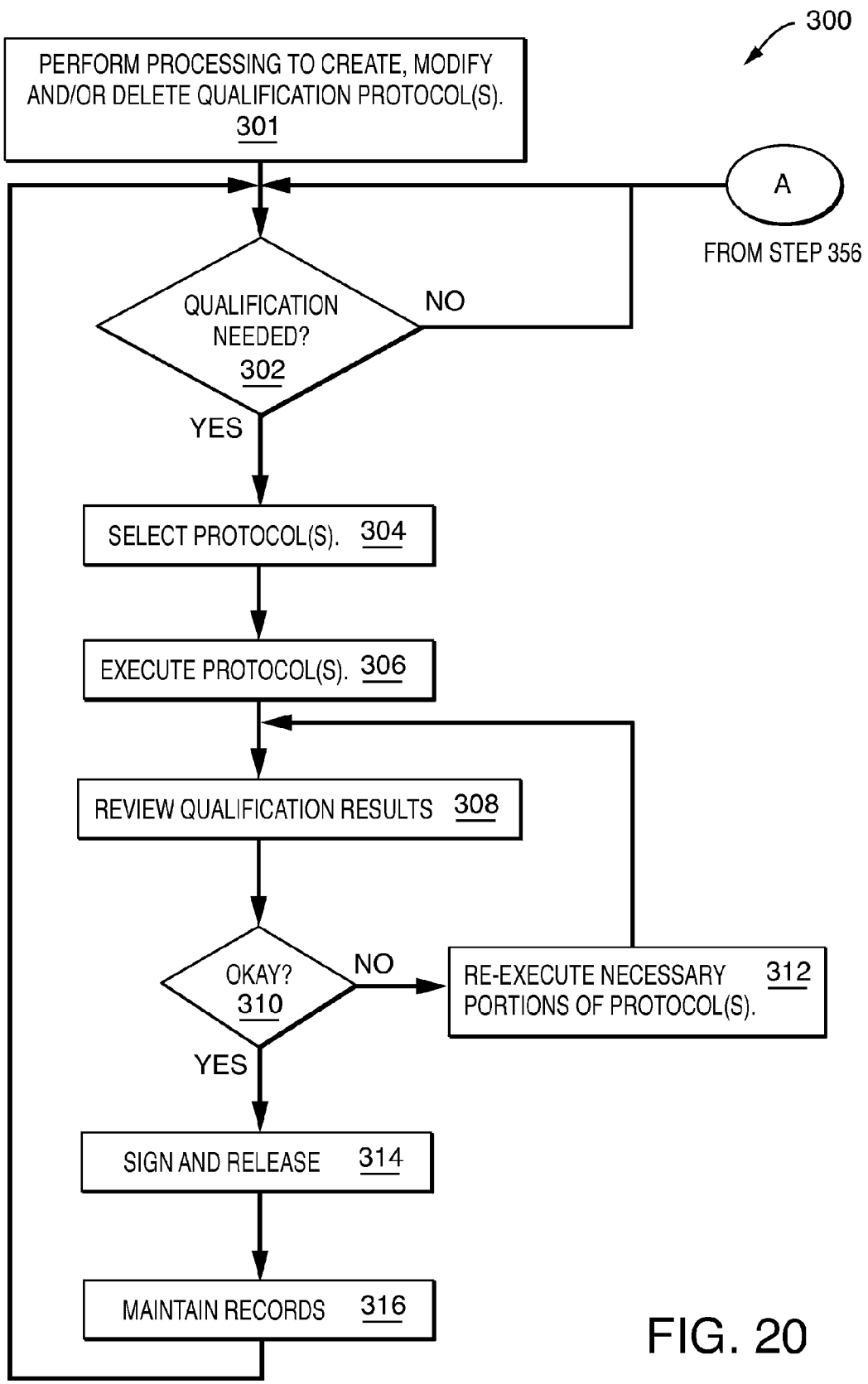

Referring to FIG. 20, shown is a flowchart of processing steps as may be performed in an embodiment in accordance with techniques herein. The flowchart 300 includes processing steps as may be performed in a typical workflow in an embodiment in accordance with techniques herein. At step 301, processing may be performed to create, modify and/or delete one or more qualification protocol(s) and associated qualification structures, also referred to herein as the qualification protocol structure or template. At step 302, a determination may be made as to whether qualification of an existing instrument system or software is needed. Step 302 may include, for example, determining whether an existing instrument system or computer requires requalification for any one of a variety of different reasons. If not, processing may remain at step 302 until such time qualification is necessary. It should also be noted that, although not illustrated, processing may also proceed from step 302 to 301 depending on whether there is a need to perform qualification protocol processing of step 301 prior to executing a defined qualification protocol. If step 302 evaluates to yes, control proceeds to step 304 to select one or more existing qualification protocols which are executed in step 306. At step 308, the results of executing the selected protocol(s) from step 306 are reviewed. At step 310, a determination is made as to whether the qualification results are approved. Step 310 may include examining the results and determining whether all tests in the selected protocol(s) have been passed. If step 310 evaluates to no, processing proceeds to 312 to re-execute necessary portions of the selected protocol(s). For example, a single protocol may include performing 4 tests and the results indicated that 3 tests passed and 1 test failed. As a result, step 312 may include performing all tests of the protocol or only the single failed test. From step 310 control proceeds to step 308. If step 310 evaluates to yes, control proceeds to step 314 where any required signoff approvals regarding the qualification results are obtained. At step 316, records in connection with the qualification results, sign-off approval, and the like, may be maintained in the database. From step 316, control may proceed to step 302. In a manner similar to that as described above regarding step 302, although not illustrated, processing may also proceed from step 316 to 301 depending on whether there is a need to perform qualification protocol processing of step 301 prior to executing a defined qualification protocol.

Figure 21:
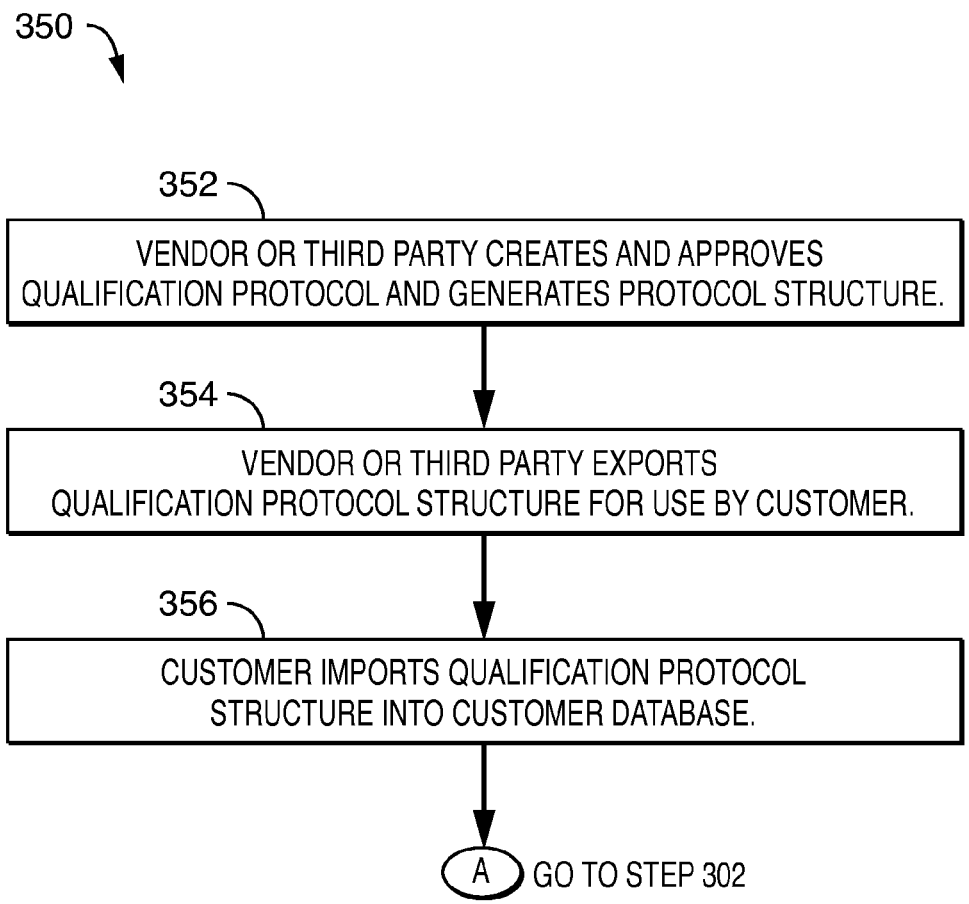

Referring to FIG. 21, shown is a flowchart 350 of processing steps that may be performed in an embodiment in accordance with techniques herein. At step 352, a vendor or third party may create and approve a qualification protocol and generate the associated qualification protocol structure or template. At step 354, the vendor or third party may export the qualification protocol structure for use by its customers. At step 356, the customer may import the qualification protocol structure into the customer's database. Control may proceed to step 302 of flowchart 300 where the qualification protocol structure may be used in connection with executing tests of the qualification protocol associated with the structure.

It should be noted that the techniques herein may be further extended to generate and use a qualification protocol structure or template that also includes other information related to other aspects of qualification such as, for example, the recommended frequency for performing re-qualification, criteria used to evaluate and determine when to perform requalification (e.g., criteria as may be related to risk of performing a particular action such as a repair or maintenance activity, system complexity and other metrics to help the software decide when to perform automated requalification or provide for user notification regarding the same), and the like.

In one embodiment described above, functionality is described using a qualification protocol framework providing for creation, modification and/or deletion of qualification protocols. The foregoing operations may be performed using qualification protocols having corresponding structures or templates stored in a database. Additionally, the database may maintain and audit records corresponding to any operations performed with respect to qualification protocols. Additionally, qualification protocols in accordance with techniques herein may be reviewed and approved by knowledgeable individuals such as by having such individual user apply an electronic signature to a qualification protocol once approved. An embodiment may also restrict access to the software used in connection techniques herein through commercialization licenses and user permissions also defined in the system.

As described herein, a qualification protocol structure or template may be exported from a database, such as from a vendor site that produced the structure, and then imported into a customer's database. When imported, processing may be performed to verify the data integrity of the structure and the authenticity of the vendor that produced the structure. Furthermore, as also described above, each qualification protocol structure may identify a signature method used at the customer's site when executing a qualification protocol. The signature method may define the review and approval sequence used as part of processing for a qualification protocol to perform and then validate the results of a qualification run. Each qualification protocol may include an IQ test sequence and a corresponding OQ/PQ test sequence. Each test in the IQ and OQ/PQ sequence may be associated with a report method (e.g., to generate a report based on test results) and a sequence of one or many analytical or non-analytical methods. The analytical methods as described herein may use an analysis method and a sample list or set. A non-analytical method may communicate with the acquisition framework (e.g., 2006 of FIG. 2B) or the qualification and maintenance center 2002. For each method, the qualification protocol structure may include data used to specify or otherwise obtain specific limits such as may be used in evaluating a particular set of test data and a method to perform the validation.

It should also be noted that embodiments are described herein with data systems and scientific instruments such as may be used in connection with sample analysis. More generally, the techniques herein may be used in embodiments with any type of instrument or other device, as well as in connection with other software systems.

The techniques herein may be performed by executing code which is stored on any one or more different forms of computer-readable media. Computer-readable media may include different forms of volatile (e.g., RAM) and non-volatile (e.g., ROM, flash memory, magnetic or optical disks, or tape) storage which may be removable or non-removable.

While the invention has been disclosed in connection with preferred embodiments shown and described in detail, their modifications and improvements thereon will become readily apparent to those skilled in the art. Accordingly, the spirit and scope of the present invention should be limited only by the following claims.

What is claimed is:

1. A method for performing qualification protocol testing comprising:
performing first processing to create a qualification protocol structure for a qualification test protocol used to qualify any of software and an instrument system, said first processing including:
selecting, using a user interface, a qualification entity category indicating a category of an entity for which the qualification test protocol is being created, wherein the qualification entity category is any of software and an instrument system;
selecting, using the user interface, one or more qualification tests included in the qualification test protocol;
specifying, using the user interface, test information for said one or more qualification tests, said test information including first information identifying one or more code modules executed to perform said one or more qualification tests, second information identifying test inputs to said one or more code modules, and third information specifying how to evaluate tests results from executing each of said one or more qualification tests;
generating the qualification protocol structure including said test information; and
storing the qualification protocol structure in a database; and
performing second processing to qualify any of software and an instrument system by using the qualification protocol structure to execute the qualification test protocol, said second processing including:
receiving the qualification protocol structure from the database; and
executing a first code module that receives and interprets the qualification protocol structure as a runtime input to drive execution of the one or more qualification tests identified in the qualification protocol structure, said first code module transferring runtime control to the one or more code modules identified in the qualification structure and then, after completing execution of the one or more code modules, returning runtime control to the first code module.

2. The method of claim 1, wherein executing said qualification test protocol includes executing the one or more qualification tests, and wherein said second processing includes generating test results in accordance with executing said one or more qualification tests.

3. The method of claim 2, wherein executing said one or more code modules identified in said first information uses said second information as inputs when executing said one or more code modules.

4. The method of claim 3, further comprising evaluating said test results, said evaluating using said third information to determine a testing status of pass or fail for each of said one or more qualification tests.

5. The method of claim 2, wherein the qualification entity category identifies said instrument system.

6. The method of claim 5, wherein said instrument system comprises a plurality of modules and the qualification protocol structure includes fourth information describing a configuration of said instrument system including said plurality of modules.

7. The method of claim 5, wherein said instrument system is a scientific laboratory instrument system that performs any of liquid chromatography, gas chromatography, mass spectrometry, supercritical fluid chromatography, capillary electrophoresis, and analog to digital signal conversion and/or transmission.

8. The method of claim 2, wherein said test information identifies one or more tests which are mandatory and one or more tests which are not mandatory and wherein the method includes deselecting at least one test that is not mandatory causing said second processing to not execute processing for said at least one deselected test.

9. The method of claim 2, wherein the qualification entity category identifies software installed on a computer system and the qualification test protocol includes one or more qualification tests for qualifying said software.

10. The method of claim 1, wherein said test information includes information identifying code to generate a report regarding evaluation of test results.

11. The method of claim 1, wherein said qualification protocol structure is bundled with any of a new software component and an updated software component, said qualification protocol structure used to perform qualification testing for any of said new software component and said and updated software component.

12. The method of claim 11 wherein said new or said updated software component is a driver used for communicating to an instrument system to operate said instrument system.

13. The method of claim 1, wherein the qualification protocol structure is approved by electronically or digitally signing the qualification protocol structure.

14. The method of claim 13, wherein the qualification protocol structure is exported from a first database on a first computer system and imported into a second database on a second computer system.

15. The method of claim 14, wherein the qualification protocol structure is encrypted producing an encrypted structure, and the method further includes:
digitally signing the encrypted structure; and
processing the digitally signed encrypted structure at the second computer system, said processing including decrypting the digitally signed encrypted structure thereby generating the qualification protocol structure and importing the qualification protocol structure into a second database on the second computer system.

16. A computer readable medium comprising code stored thereon that, when executed, performs a method of qualification protocol testing comprising:
performing first processing to create a qualification protocol structure for a qualification test protocol used to qualify any of software and an instrument system, said first processing including:
selecting, using a user interface, a qualification entity category indicating a category of an entity for which the qualification test protocol is being created, wherein the qualification entity category is any of software and an instrument system;
selecting, using the user interface, one or more qualification tests included in the qualification test protocol;
specifying, using the user interface, test information for said one or more qualification tests, said test information including first information identifying one or more code modules executed to perform said one or more qualification tests, second information identifying test inputs to said one or more code modules, and third information specifying how to evaluate tests results from executing each of said one or more qualification tests;
generating the qualification protocol structure including said test information; and
storing the qualification protocol structure in a database; and
performing second processing to qualify any of software and an instrument system by using the qualification protocol structure to execute the qualification test protocol, said second processing including:
receiving the qualification protocol structure from the database; and
executing a first code module that receives and interprets the qualification protocol structure as a runtime input to drive execution of the one or more qualification tests identified in the qualification protocol structure, said first code module transferring runtime control to the one or more code modules identified in the qualification structure and then, after completing execution of the one or more code modules, returning runtime control to the first code module.

17. A system comprising:
a plurality of scientific instruments;
one or more computer systems used to control and/or communicate with the plurality of scientific instruments;
a computer readable medium comprising code stored thereon that, when executed, performs a method for qualification protocol testing comprising:
performing first processing to create a qualification protocol structure for a qualification test protocol used to qualify any of software and an instrument system, said first processing including:
selecting, using a user interface, a qualification entity category indicating a category of an entity for which the qualification test protocol is being created, wherein the qualification entity category is any of software and an instrument system;
selecting, using the user interface, one or more qualification tests included in the qualification test protocol;
specifying, using the user interface, test information for said one or more qualification tests, said test information including first information identifying one or more code modules executed to perform said one or more qualification tests, second information identifying test inputs to said one or more code modules, and third information specifying how to evaluate tests results from executing each of said one or more qualification tests;

generating the qualification protocol structure including said test information; and storing the qualification protocol structure in a database; and performing second processing to qualify any of software and an instrument system by using the qualification protocol structure to execute the qualification test protocol, said second processing including:

receiving the qualification protocol structure from the database; and executing a first code module that receives and interprets the qualification protocol structure as a runtime input to drive execution of the one or more qualification tests identified in the qualification protocol structure, said first code module transferring runtime control to the one or more code modules identified in the qualification structure and then, after completing execution of the one or more code modules, returning runtime control to the first code module.

* * * * *